(12) United States Patent
Fiekowsky

(10) Patent No.: US 6,263,292 B1
(45) Date of Patent: Jul. 17, 2001

(54) HIGH ACCURACY PARTICLE DIMENSION MEASUREMENT SYSTEM

(76) Inventor: Peter J. Fiekowsky, 952 S. Springer Rd., Los Altos, CA (US) 94024

(*) Notice: Subject to any disclaimer, the term of this patent is extended or adjusted under 35 U.S.C. 154(b) by 0 days.

(21) Appl. No.: 09/028,207

(22) Filed: Feb. 23, 1998

Related U.S. Application Data

(63) Continuation-in-part of application No. 08/807,789, filed on Feb. 28, 1997.

(51) Int. Cl.$^7$ .................................................. G03B 27/42
(52) U.S. Cl. ............................ 702/95; 702/159; 356/241
(58) Field of Search ...................... 702/95, 159; 355/53, 355/67–69; 356/254, 241, 429, 430

(56) References Cited

U.S. PATENT DOCUMENTS

| | | | |
|---|---|---|---|
| 5,614,990 | 3/1997 | Bruce et al. | 355/71 |
| 5,804,336 | 9/1998 | Rolfon | 430/5 |
| 5,966,677 | 10/1999 | Fiekowsky | 702/95 |

OTHER PUBLICATIONS

Tran et al., "Application of image processing software to characterize the photomask key parameters for future technologies" Processings of the SPIE–The international Society for Optical Engineering, vol. 3096, p 423–432, Apr. 1997.*
George et al., "A practical and Precise Method for Mask Defect Size Measurement", Mar. 10, 1996, Proceedings of the SPIE Conference on Photo–Lithography.
Stocker et al., "Characterization of Defect Sizing on an Automatic Inspection Station (KLA 238e)", 1993, SPIE vol. 2087 Photomask Technology and Management.
Kawahira et al. "SEMI Standards Programmed Defect Masks and it's Applications for Defect Inspection", SEMI Japan Standards Committee No Date.

Peter J. Feikowsky, Quotation (Preliminary), Oct. 17, 1994; "Klaziq Photomask Defect Inspecting System (Phototype System)".

(List continued on next page.)

*Primary Examiner*—Kamini Shah
(74) *Attorney, Agent, or Firm*—Beyer Weaver & Thomas, LLP

(57) ABSTRACT

A measurement tool connects to a microscope which may be an automatic inspection machine for identifying and measuring microscopic dimensions of features on a photographic mask such as opacity, area, diameter, width, height, line widths and corner radius. Dimensions of features having sizes of less than about twice the wavelength being used (less than 1 micron for visible light) are measured quickly and accurately in a production environment. The opacity of a feature is determined and used for correcting area or height measurements as well as helping to determine what the feature is made of. A contrast vs. diameter curve for known opaque features is used to determine opacity of unknown features. The curvature of the intensity profile of the feature is used in conjunction with a curvature-width lookup table in order to produce the width of the feature. Curvature-width lookup data is developed from the area and diameter of known round defects along with the curvature of the profile of the round defects. A width-height multiplier is used to correct the measured height due to the blurring associated with sizes of features close to the wavelength being used. An opacity correction is also used to correct the height of features that are less than 100% opaque. Width-height multiplier data is developed by measuring the area and diameter of known round defects, measuring their height and computing a multiplier. An actual measurement of the height of a feature measures both the height and the width. Width-height multiplier data is referenced using the measured width to produce a height multiplier for that width. The radius of curvature is also determined at submicron sizes using a flux measurement.

21 Claims, 28 Drawing Sheets

OTHER PUBLICATIONS

Tran et al., Application of Unage Processing Software to Characterize the Photomask Key Parameters; SPIE vol. 3096 Apr. 17–18 1997.

Fiekowsky et al., "Defect printability measurement on the KLA–351: Correlation to Defect Sizing using the AVI Metrology System", SPIE 19$^{th}$ Annual BACUS Symposium on Photomask Technology and Management Conference 3873, Sep. 1999.

* cited by examiner

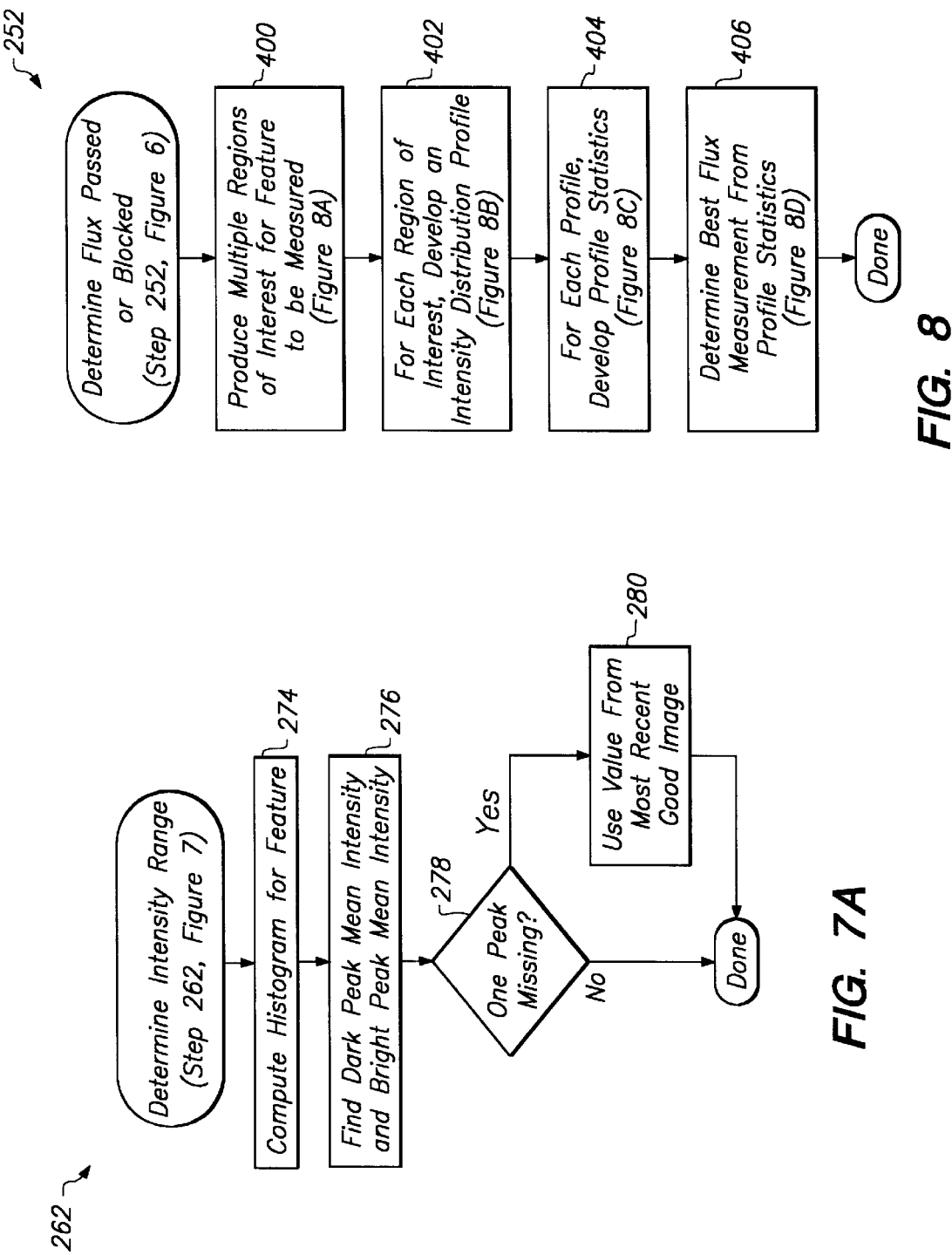

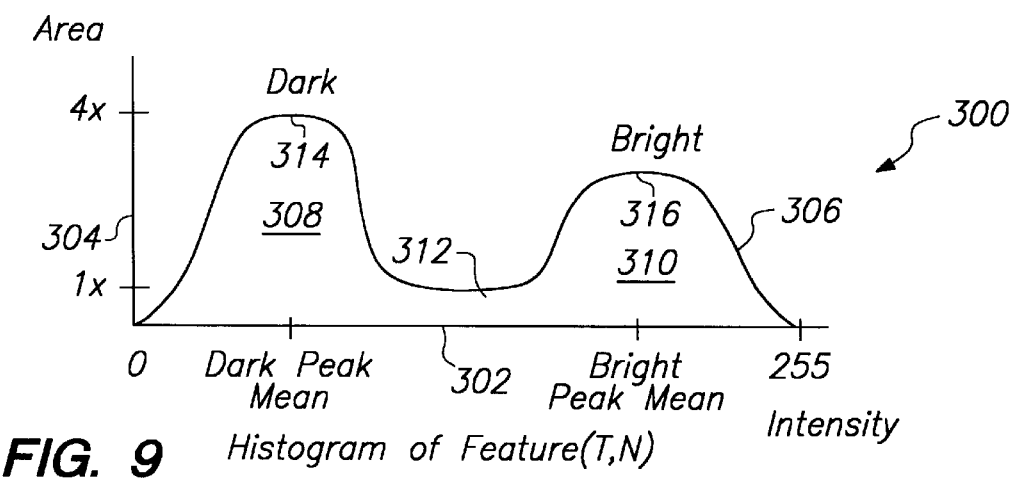
FIG. 9 Histogram of Feature(T,N)
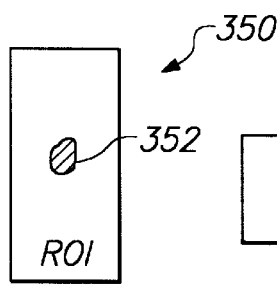
FIG. 10A
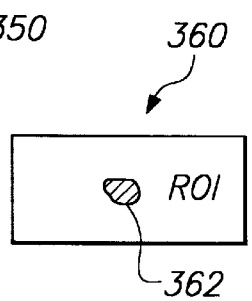
FIG. 10B
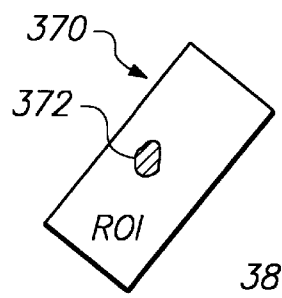
FIG. 10C
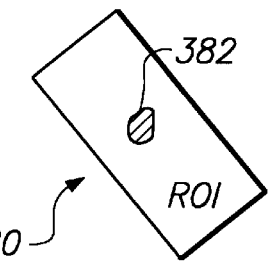
FIG. 10D
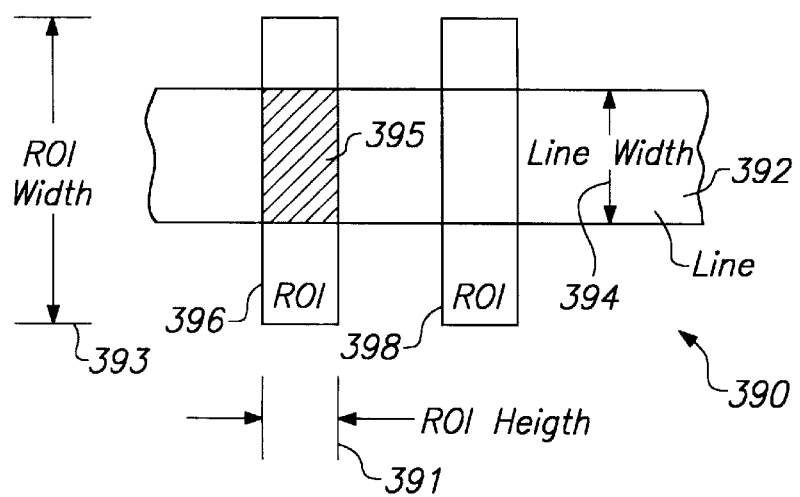
FIG. 10E

Intensity Distribution Profile

Profile

Profile

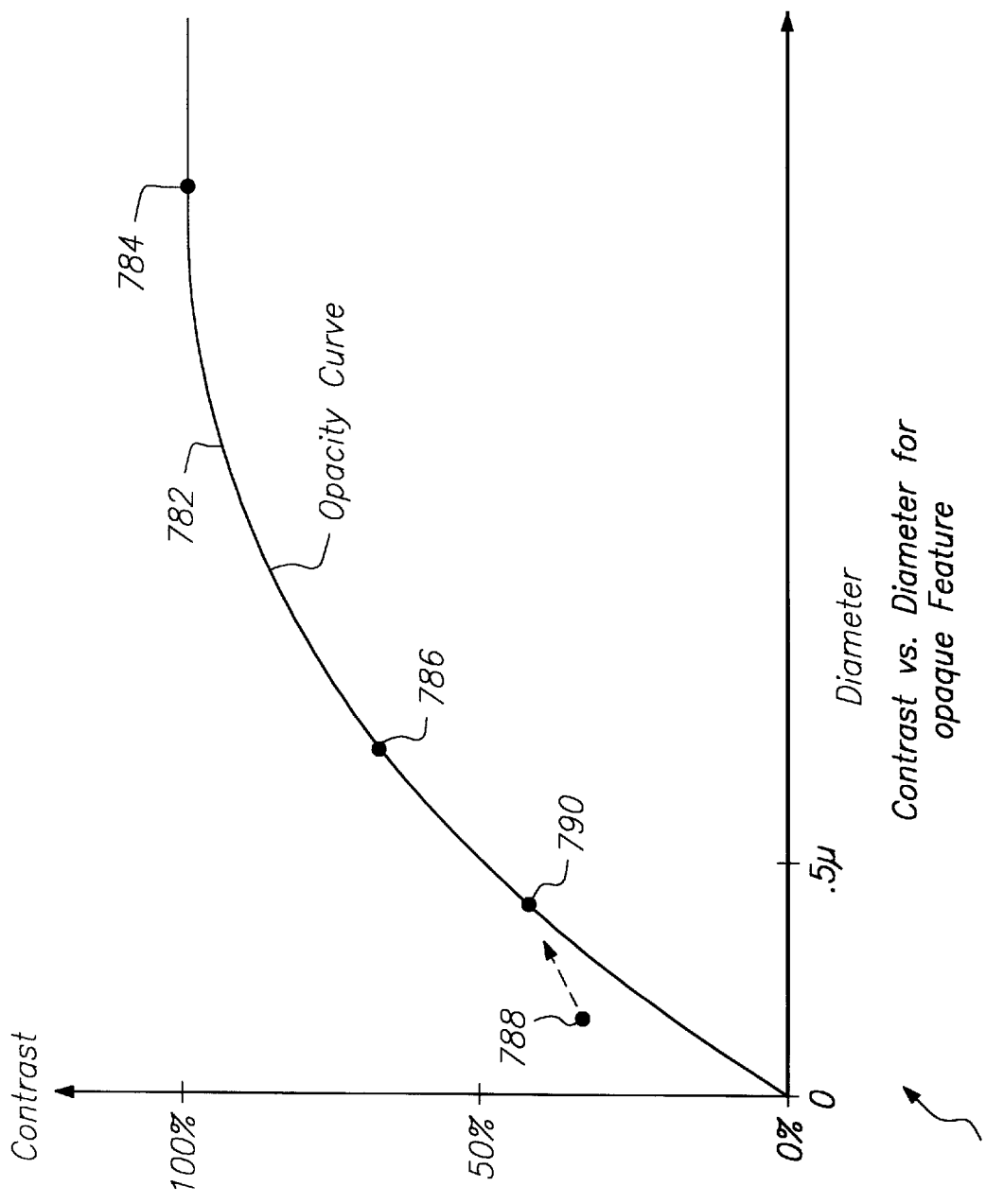

HIGH ACCURACY PARTICLE DIMENSION MEASUREMENT SYSTEM

This application is a continuation-in-part of U.S. patent application No. 08/807,789 filed on Feb. 28, 1997 in the name of Peter J. Fiekowsky and which is incorporated by reference.

FIELD OF THE INVENTION

The present invention relates generally to computer measurement systems. More specifically, the present invention relates to the measurement of features on photographic masks used in semiconductor manufacturing.

BACKGROUND OF THE INVENTION

The recent introduction of advanced sub-micron sized semiconductor devices require reduced critical dimensions and increased packing densities. At these sub-micron sizes and high densities, even defects and imperfections as small as 1 micron and below are problematic and need to be detected and evaluated. Imperfections in the reticle generated by a photographic mask manufacturing process are one source of defects. Errors generated by such a photomask manufacturing process have become an important issue in the manufacture of semiconductor devices at these sub-micron sizes. Defect inspection techniques for masks are therefore becoming to play a more important role in mask making and quality assurance.

Thus, it is becoming increasingly important to be able to identify and to correctly size mask defects, line widths, heights of edge defects and other features that are under 1 micron in size. Accurate sizing of these features allows masks that are below specification to be repaired, and prevents the needless and costly hold up of masks that do meet specification. However, one of the problems of assessing reticle quality at these submicron levels on an automatic inspection system is that the size of these features cannot always be accurately, quickly and cost-effectively measured in a production environment.

Although mask makers typically repair most defects found at early inspection stages, invariably, defects are found at later inspection stages (such as after pelliclization of the mask has occurred). These late stage defects are sized and classified relative to a defect size specification, the size at which device performance is deemed to be affected.

Currently, defects found by automatic inspection tools are classified in one of the following categories by a human operator: (1) a real defect is a hard or soft defect that exceeds the defect size specification, (2) a sub-specification defect is a random or process-related defect below specification that is within a safety margin, and (3) a false defect is a defect detected by the inspection tool with no apparent cause.

Classification of the above types of defects is largely a subjective activity based upon operator skill. However, as defect size specifications diminish, the distinction between real and sub-specification defect classification has become increasingly difficult. For example, as the line width on sub-micron masks approaches 0.1 micron, the ability to measure defect sizes at 1 micron and below becomes very important. Current production machines have an accuracy of 0.1 micron to 0.2 micron, but this is not sufficient.

It has long been known that mask inspection tools are not measurement tools and that the size information provided by these tools has limited value for measurement-based defect classification. Consequently, many mask makers have incorporated measurement aids at the inspection station or have moved the mask to a more suitable measurement tool in order to make classification decisions. Measurement aids used at the inspection station include calipers, grids, and software based video image markers such as gates, scales, grids, boxes and circles. These aids are fairly rapid, but ultimately require the operator to "eyeball" the boundaries of the defect. This activity is very subjective and can lead to an error in the measurement of the defect.

For example, particle size is conventionally measured by measuring the distance between opposite edges of the particle. Once a defect is identified by an inspection machine, the operator uses a video microscope and a television camera to position a cursor on one side of the defect and another cursor on the other side of the defect. The operator must judge for himself the exact boundaries of the defect and must place the cursors where he sees fit. At this point, the operator pushes a button and the software blindly computes the distance between the two cursors in order to supply a rough approximation of the diameter of the defect. This technique has many disadvantages.

Firstly, this measurement technique is operator dependent in that the operator must manually position the cursors on the boundaries of what the operator believes to be the defect. The operator may misjudge the type of a defect, its boundaries, or may simply misplace a cursor even if the defect is visible. The software then blindly calculates the distance between the cursors, without regard for the type of defect, its true boundaries, etc. The above technique may be performed with a standard video microscope and has an accuracy of about 0.1 micron, but is completely subject to the operator's skill level and interpretation. This technique is also unable to calculate an area for a defect.

Another difficulty with light measurements of features less than 1 micron in size is that the wavelength of photons begins to interfere with the measurement of these smaller and smaller feature sizes. Current techniques do not adequately address the non-linearities associated with such measurements.

Alternatively, the mask may be removed from the automatic inspection tool and relocated on a more precise and repeatable measurement tool. However, this approach involves removing the mask from production, relocating the defect, and is thus impractical in a production environment. This technique is also costly, time-consuming and increases the handling risk. For example, an atomic force microscope (AFM) may be used to measure defect sizes; such a microscope is extremely accurate but is very slow, very expensive and is still subject to operator interpretation.

One approach that has been taken that uses calibration of an automatic inspection system in order to size defects is described in "Characterization Of Defect Sizing On An Automatic Inspection Station", D. Stocker, B. Martin and J. Browne, Photomask Technology and Management (1993). One disadvantage with the approach taken in this paper is that it only provides a technique for measurement of defects of 1.5 microns and greater. Such sizes of defects would produce a linear relationship between reference sizes and actual measured sizes, and the paper does not account for defects less than 1 micron that would produce a non-linear relationship. Also, the technique does not allow for individual calibration data for particular types of defects.

Therefore, an objective feature measurement tool is desirable for use with a photomask inspection tool that can provide reliable and repeatable measurements of defects and other features of less than about one to two times the microscope resolution (or about less than one micron for optical microscopes). It would be especially desirably for such a tool to operate in a fast and highly practical manner in a production environment.

Furthermore, at subresolution sizes it can be extremely desirable to determine the opacity of a feature or defect. For example, measurement of the area or other dimension of a feature will be affected if the feature is not 100% opaque. That is, features that are less than opaque make flux-based measurements of area, diameter, height and/or other dimensions more difficult. For example, a light measurement of a half-transparent spot defect produces more flux from the defect than a perfectly opaque defect; thus, a measured area would appear to be about one-half of the true area. In other words, a less than 100% opaque feature would appear smaller than it truly is. It would be desirable to determine the opacity of the feature or defect to not only correct for a measured dimension of the feature, but also to help determine what the feature is composed of. It would be especially useful to determine the opacity of features having a size that are less than about twice the wavelength being used.

As previously explained, it is desirable to be able to measure the area, and hence the diameter of a feature or defect that is extremely small. Measurement of diameter in this fashion is especially useful when the feature is round, or when it can be assumed that the feature is round. However, features and defects are not necessarily always round; for example, features of about less than 1 micron in size may appear round when in fact they are not due to the blurring effect. In a variety of situations, it can be important to know more specific dimensions of a feature if the feature is not round. For example, given two aluminum lines on a silicon substrate, an edge defect in one line might produce a short across to the other line. However, measurement of the area of this edge defect (to produce an estimated diameter) will not necessarily indicate that the edge defect is in danger of shorting out the two lines. This is because a rather elongated edge defect that is in no danger of shorting the two lines will have the same area as a narrower, taller defect that may in fact produce a short. Determination of the diameter of a defect by measurement of the area of the defect may not always indicate the true height or width of a defect, especially if the defect is not round.

Traditionally, a deconvolution technique using a Fourier transform to a frequency space has been used to measure height and width of features that are less than 1 micron in size. However, this technique has typically not produced accurate results for features of this size. Therefore, in order to more accurately classify features and defects it would be useful to be able calculate the height and width of a feature or defect with a high accuracy. Determination of height and width of features having sizes that are less than about twice the wavelength being used would be especially useful.

It would also be desirable to be able to determine the radius of curvature of a corner of a line, especially at sizes that approach, or are less than, the wavelength of light or the particle beam being used where blurring is a problem.

SUMMARY OF THE INVENTION

The present invention discloses a measurement tool that provides an objective, practical and fast method for accurate sizing of mask features found with an automatic inspection tool (such as a video inspection machine). Diameters of defects and dimensions of other features can be measured by using gray scale image information provided by the automatic inspection tool. The present invention may be used while the photomask is in-place at the inspection station, and there is no need for the mask to be removed to a different machine for measurement. Also, an operator is able to quickly outline a general region around a feature to be measured without the need for the operator to judge the size of the feature. The dimension of the feature is then automatically identified and measured quickly by the measurement tool of the present invention.

Benefits include avoiding repairing masks within specification, and equivalent results whether measured by customer or supplier (when calibrated with the same reference). Also, marginal defects are accurately measured and classified as fatal or not, and sub-specification defects are stored and documented with printouts including picture and text. Operator productivity and tool utilization is improved by rapid measurements taking place at the inspection station. Repair quality may also be checked by taking a line width measurement.

The disclosed measurement tool objectively and repeatedly measures defects (spots, holes, intrusions, extensions, etc.), line widths at any angle (transmissive and opaque vertical and horizontal lines), heights of edge defects and dimensions of a variety of other features for determining photomask disposition. The measurement tool operates automatically and is not dependent upon operator judgement. Defects from 0.1 to 1.5 microns can be measured, repeatable to 0.02 microns and accurate to 0.05 microns with a typical AFM calibration. Line widths less than 1 micron can be measured, repeatable to 0.05 microns and accurate to 0.1 micron with a typical AFM calibration. Measurements from an AFM, Vickers or OSI machine may be simulated by calibrating to their standards. Additionally, the measurement tool provides automatic measurements in 1 to 5 seconds (including operator actions).

By analyzing a VERIMASK image and correlating measured pixel widths of the feature to the known size of the defect or line width in microns, the inspection machine, its optics and electronics, video hardware, and computer hardware and software may all be calibrated. There is no need to calculate variances due to individual camera response, ambient light, individual machine characteristics, or other variables. Thus, a measurement of an actual defect (for example) using the same hardware to return a diameter in pixels may be directly compared to a particular calibration curve for that type of defect in the calibration database in order to return an extremely accurate width of the defect in microns.

In one embodiment, test features of known sizes (measured from a VERIMASK, for example, a plate with programmed features and standard sizes for each feature, made by DuPont Photomasks Inc., of Round Rock, Tex.) are first measured in order to serve as a calibration gauge for the measurement tool. Once dimensions in pixels for these features have been determined, these measured dimensions for various sizes of features are plotted against the true sizes in microns of the features (known beforehand). This calibration procedure yields a polynomial curve that is used for future measurements of features of unknown sizes on the same hardware, in order to calibrate the measurements. In a further embodiment, a separate calibration curve is developed for each type of defect and for each variety of line width. Separate calibration curves for each feature correct for optical characteristics of the system in relation to a particular feature and likely skews in the reference measurements due to individual features.

In another embodiment of the invention, a non-linear calibration polynomial curve is produced relating measured sizes of features from a particular machine to known reference sizes of these features. A light measurement is performed on features of unknown sizes on the same machine to return a measurement in pixels. This value in pixels may then be compared to the above described calibration curve in order to return an accurate value of the size of the feature in microns. In a further embodiment, calibration curves are developed for each type of feature, and light-measured features of a particular type are compared to their specific calibration curve. Advantageously, a calibration curve yields a more accurate measurement.

In another embodiment of the invention, the type of a feature is determined by first forming a bounding box around the feature. Analysis of whether the box touches a user region of interest yields either an isolated defect or other feature. Analysis of light transitions for other features yields a determination of the types of these other features. The feature type is determined automatically.

In yet another embodiment, a good quality source image of a feature is found by subtracting a reference image. A light intensity distribution profile is first developed for a region surrounding the feature. If the profile is not of good quality, then a reference image of the feature is obtained and subtracted from the feature image in order to produce a good quality source image.

In another embodiment of the invention, multiple regions of interest are formed surrounding a feature and an intensity profile is developed for each region of interest. A total light flux measurement is calculated for each profile, and one of the light flux measurements is chosen as the best flux value. A good quality profile is chosen such that the total flux measured from the profile is proportional to the area of the defect. Multiple regions allow for angled lines.

In a further embodiment of the invention, a region of interest surrounds the feature and a profile for the feature is produced by summing columns of pixels across the feature site in the region of interest. A baseline intensity value is determined for the profile and is subtracted from the profile in order to determine the total flux passing through the feature. Subtraction of a baseline removes background intensities and obviates the need to obtain a reference image.

In yet another embodiment, the height of edge defects may be measured accurately. The height of a defect is important to measure especially if the defect occurs on an edge, such as a bump on a line or a bite into a line. The height refers to the two-dimensional distance that an extension sticks out from a line, or how far an intrusion bites into a line (as opposed to the three-dimensional thickness of a defect). The measurement of height provides an indication of how close the defect extends to adjacent lines in two dimensions. One column of light intensities one pixel wide in the profile is summed to determine an area of the feature that corresponds to the height of the feature.

In a further embodiment of the invention for calculating line width, a region of interest surrounds a line portion and a profile for the line portion is produced by summing columns of pixels across the line portion in the region of interest. The total flux is then determined for the profile and is used to find the area of the line portion,. The area of this line portion divided by a dimension of the region of interest yields the line width.

In another embodiment, calibration data is developed for a line in order to calculate a line width. A light measurement is taken of a line width of known size that is at a distance of less than one resolution unit from another line. A full-width half-maximum technique is used to assist in calculating the line width. The measurements are repeated for number of line widths of different sizes in order to develop calibration data that relates light-measured values for line widths to the known widths of the lines. The calibration data may be represented as a non-linear polynomial curve that can be referenced by future measurements of line widths of unknown sizes that are less than one resolution unit from other lines in order to return more accurate results.

In one other embodiment, non-linear calibration data is developed for line widths of lines that are less than one resolution unit from other lines. An actual measurement of a line width of unknown size that lies less than one resolution unit from another line may reference the calibration data in order to return a more accurate result. The use of calibration data developed using a full-width half-maximum technique is advantageous for lines less than one resolution unit apart due to non-linearities associated with measurements at these small dimensions.

In an additional embodiment, an image of a feature is extracted from the video output of an automatic inspection tool. The operator draws a very rough box around the general feature site without needing to gauge the size of the defect. Pin point accuracy is not needed. The measurement tool automatically picks out the feature from within the region of interest identified by the operator, identifies the feature, and calculate the area, width and height of the feature. These measurements are completely independent of the size of the region of interest identified by the operator, thus removing operator judgement from the measurement.

Thus, by providing an extremely accurate measurement of mask features, the disclosed measurement tool helps to avoid unnecessary mask repairs and allows for improved process control. Also, operator variability is eliminated, and overall productivity and mask throughput is increased due to the accurate measurements in-place and documentation produced in seconds. Because the measurements are automatic, operator training is minimal. Repair quality can also be quickly checked by using line width measurements.

In another specific embodiment, the present invention determines the opacity of a feature or defect to use in correcting area or height measurements as well as helping to determine what the feature is made of. While prior art techniques may produce opacity values for relatively large particles, the present invention is especially useful for dimension measurements of less than perfectly opaque features that are under 1 micron in size.

The present invention is also able to measure specific dimensions (such as height and width) of features that are under about one to two times the microscope resolution. Features and defects such as spots, holes, line widths, edge defects, etc., can all be accurately sized at this subresolution size even though blurring is present. The prior art has had difficulties in measuring the width of a feature at subresolution sizes. In a specific embodiment of the invention, the curvature of the intensity profile of the feature is used in conjunction with a curvature-width lookup table in order to produce the width of the feature. Advantageously, the present invention develops curvature-width lookup data by determining the area and then the diameter (or width) of known round defects. The curvature of the profile of the round defect is also determined. The width and curvature are then entered as a data point in the lookup table, and the process is repeated for defects of other sizes to fill out the table. Alternatively, width of a feature could be directly measured on another machine for use in the lookup table.

In another embodiment of the invention, the height of a feature is accurately determined for features having sizes less than subresolution. In one embodiment, a width-height multiplier is used to correct the height due to the blurring associated with sizes close to image resolution. An opacity correction is also used to correct the height of features that are less than 100% opaque. Width-height multiplier data is developed by measuring the area of a known round defect in order to get its diameter (or height). The height of the same defect is then measured using the techniques described herein (techniques that are applicable to defects of any shape). The height determined from the area (which is assumed to be more accurate for a round defect) is then compared to the measured height to produce a height multiplier. This process is repeated for round defects of a variety of sizes to produce the width-height multiplier data. During an actual measurement of the height of a feature of unknown dimensions, both the height and width are measured using the techniques described herein. Then the width-height multiplier data is referenced using the measured width to produce a height multiplier for that width. The height multiplier is multiplied with the measured height to produce a corrected height.

Preferably, profiles are taken parallel to lines for edge defects and nearby isolated defects. Thus, a "width" value is obtained using the curvature technique described above, and a "height" value is obtained using the height multiplier technique from above. For isolated spot defects that are about at least two blur distances from a line, a profile could be taken in any orientation and thus a "width" measurement could be used to determine both dimensions by forming profiles orthogonal to one another. Similarly, a "height" measurement could also be used to determine both dimensions for such isolated defects.

It should be appreciated that the dimensions of height and width are arbitrarily imposed on the orientation of a two-dimensional feature, and the two terms can be interchanged without effecting the operation of the present invention. In a preferred embodiment, width refers to a dimension parallel to a nearby line, while height refers to the dimension orthogonal to width.

Frequent reference is made herein to the applicability of the invention for sizes of features less than about 1 micron; this range applies to visible light, where the wavelength is about 0.5 micron. For other wavelengths, the present invention is generally suitable for features having sizes less than about two times the blur distance of the optics being used, or for features that are less than about twice the wavelength being used. The invention is especially suited for features having sizes close to or less than the wavelength being used.

An embodiment of the present invention is able to accurately determine the radius curvature of corners of features on a variety of media, and especially at subresolution sizes.

BRIEF DESCRIPTION OF THE DRAWINGS

The invention, together with further advantages thereof, may best be understood by reference to the following description taken in conjunction with the accompanying drawings in which:

FIG. 7A is a flowchart for the determine intensity range step of FIG. 7.

FIG. 8 is a flowchart for the determine flux step of FIG. 6.

FIG. 9 is a graph showing a histogram for a particular feature of a mask.

FIGS. 10A through 10D show various orientations for system regions of interest that surround a particular defect.

FIG. 10E shows two system regions of interest used for developing profiles of a line width.

FIG. 19 is a graph illustrating contrast versus diameter for an opaque material.

DETAILED DESCRIPTION OF THE INVENTION

In one embodiment of the present invention, a number of artificially produced standard features of known sizes are each measured using the measurement tool of the present invention to produce a calibration graph for each type of feature that plots the measured dimension of the feature in pixels versus the known size of the feature in microns. For each type of feature, a number of features of the same type of different sizes are analyzed in order to produce a plot fit with a polynomial curve. These artificial features may be measured in order to determine their true size by using a wide variety of techniques. By way of example, an atomic force microscope, Vickers machine or other may be used to determine the true reference size of the features.

Once the calibration graphs have been developed for each type of feature, then a particular real feature of unknown size is measured using the measurement tool of the present invention. The amount of light absorbed by the feature, or transmitted by a hole in a surface that should be opaque, is measured. This flux value is used to produce an area in pixels of the feature which can then be correlated to the actual reference size in microns of the feature by using the polynomial curve of the previously developed calibration graph for that feature type. In most cases for features smaller than 1 micron, it can be assumed that the feature is effectively circular, thus, the diameter of the feature can be computed from its area. This assumption can be justified because defects smaller than 1 micron will most often appear circular due to the defraction of light (light photons are approximately 0.5 microns in size). Additionally, such defects are typically nearly circular. Defects that are non-circular (and usually larger than 1 micron) can still be measured using the "eyeball" method with the aid of a built-in 1 micron reticle reference grid supplied. Additionally, defects that are not quite opaque are treated as if they were opaque.

A variety of lighting techniques and/or particle microscopes (such as an electron microscope) may be used with the present invention. For illustrative purposes, the present invention is described herein in connection with transmitted illumination, although the applicability of the invention is not so limited.

OVERALL SYSTEM

Figure 1:
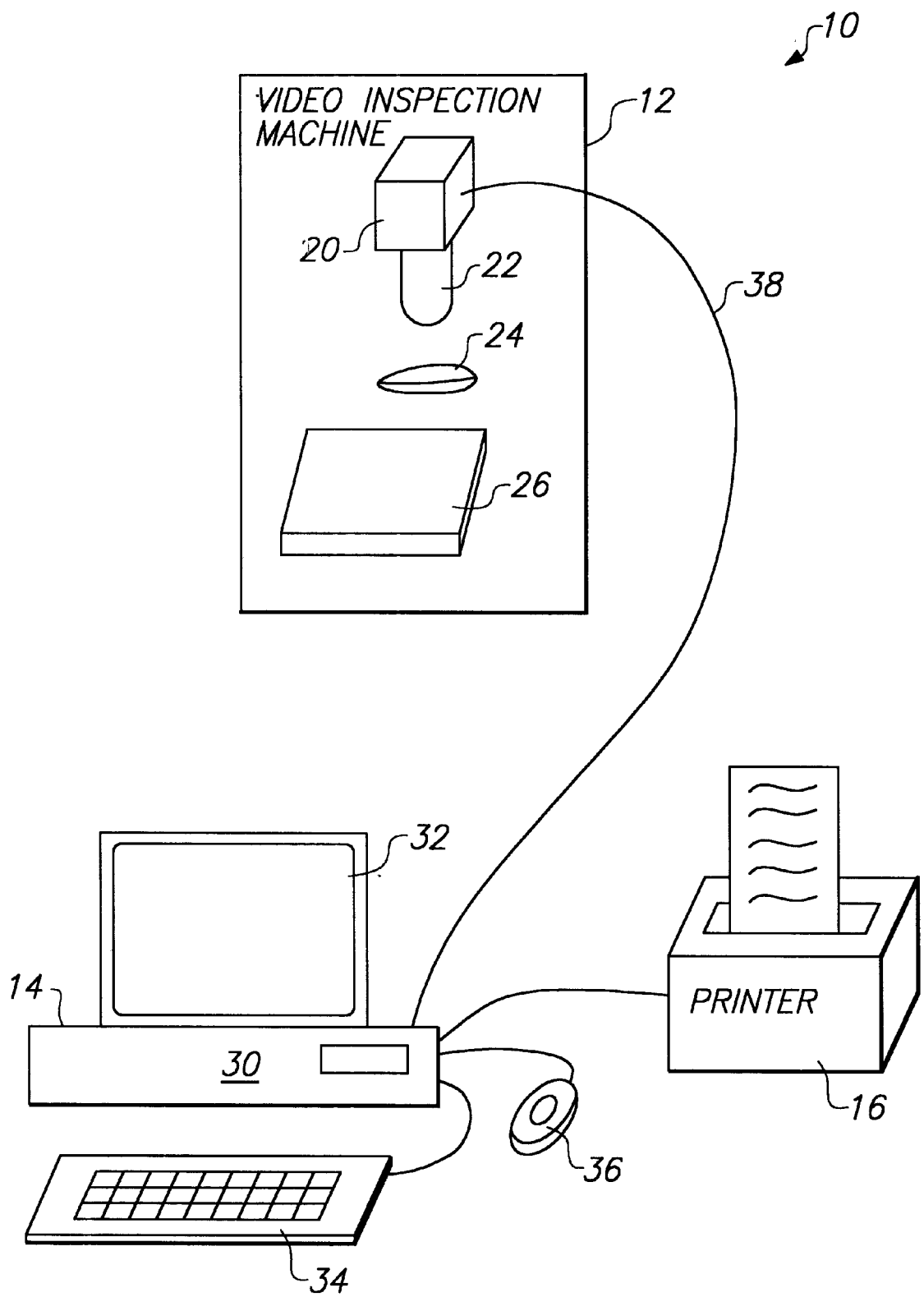
FIG. 1 illustrates a measurement system in accordance with one embodiment of the present invention.

Turning now to FIG. 1, a feature measurement system 10 in accordance with one embodiment of the present invention includes a video inspection machine 12, a computer system 14 and a printer 16. Video inspection machine 12 may be one of a wide variety of automatic inspection tools that analyze microscopic particles, lines, dimensions, etc., and outputs a video image of the microscopic features that it is analyzing. By way of example, machine 12 may be a KLA 2xx or 3xx, or DRS-1, DRS-2 automatic inspection tool used for inspecting photographic masks that are used in the manufacture of semiconductor devices. Machine 12 includes a video camera 20 having a lens tube 22 and a lens 24 that is inspecting a medium 26. Medium 26 may be one of a wide variety of media having microscopic features that are suitable for measurement by the present invention. By way of example, medium 26 is a glass reticle having a chrome pattern upon it forming a mask used in semiconductor manufacturing. Of course, other materials and substrates may be used to form the pattern of the mask. And a wide variety of other media may be suitable for use with present invention. For example, media such as a printed circuit board, other transparent media, and other types of masks may have measurements performed upon them using any of the various techniques of the present invention.

In one embodiment, a multi-camera option may be used in which two or more inspection machines of different types provide video data to the measurement tool. Each machine may use separate calibration data which is changed automatically when input is switched to originate from that machine.

Computer system 14 may be any suitable computer system for embodying the measurement tool of the present invention. By way of example, computer system 14 may be a PC computer having hardware 30, a high resolution monitor 32, a keyboard 34 and a mouse or track ball 36. Printer 16 is also connected to computer system 14 for allowing results of feature measurements to be printed.

Computer system 14 is connected to machine 12 via cable 38 which may be any suitable cable for transmitting raw video output data from machine 12 to computer system 14. In operation, machine 12 transmits via cable 38 multiplexed (in time or by position) feature image data and reference data to computer 14 for analysis and measurement. The reference data received from machine 12 is an image of what a particular portion of the mask should look like free of defects. This reference data may be retrieved from a mask database or may be obtained by doing a die to die comparison. Reference data is used when a good quality profile is difficult to obtain and will be explained in greater detail below with reference to FIG. 7. Thus, machine 12 transmits not only the results of measuring artificially produced standard features for the purpose of producing calibration data, but also transmits live video images and reference images for actual features of unknown dimensions that are identified upon mask 26.

Figure 2:
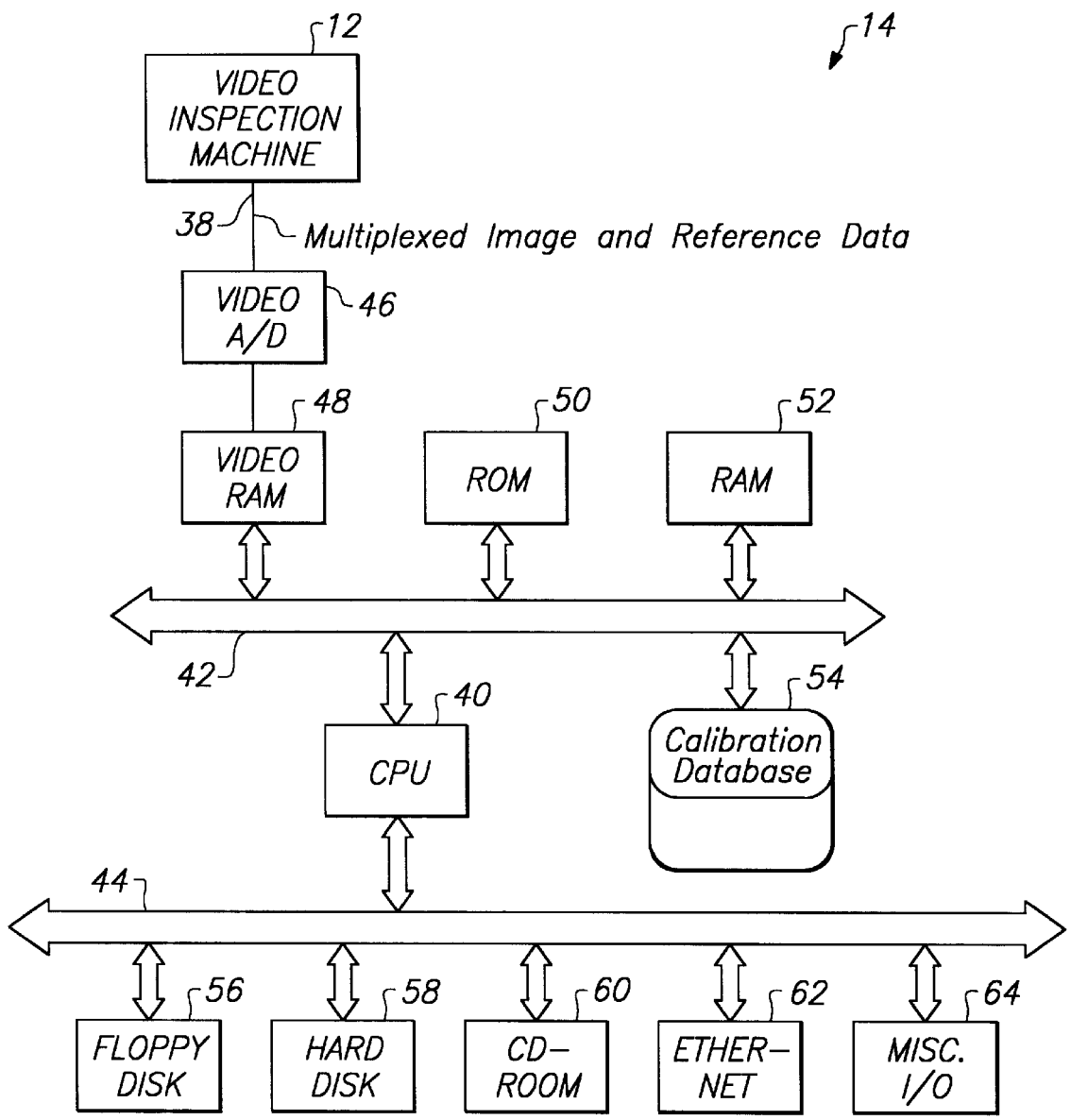
FIG. 2 is a block diagram of an embodiment of a computer system used in the measurement system of FIG. 1.

FIG. 2 illustrates in greater detail the computer system 14 of FIG. 1. A wide variety of computer configurations may be used; one alternative embodiment for a computer system 14 is shown in a later figure. Hardware 30 includes a CPU 40 connected to a PCI bus 42 and also connected to any suitable computer bus 44. Video data from machine 12 travels over cable 38 to digitizer hardware 46 that converts the video analog signal to digital form. Hardware 46 is preferably high-resolution video capture hardware.

Once the video data has been converted to digital form by digitizer 46 the digital data is stored in video ram 48. Also connected to bus 42 is read-only memory (ROM) 50 and random access memory (RAM) 52. A calibration database 54 is also accessible via bus 42 and may be contained in any suitable memory of the computer. Calibration database 54 contains individual points plotted as shown in FIGS. 16, 17 and 18, and also the equations for the polynomial curves that represent these points. The database will be explained in greater detail below with reference to FIG. 4.

Connected to bus 44 are a wide variety of input and output devices. By way of example, shown are a floppy disk 56, a hard disk 58, a CD-ROM 60, a network connection 62 in the form of an Ethernet connection, and a wide variety of other miscellaneous input and output devices 64 that include printer 16, monitor 32, keyboard 34 and track ball 36.

FEATURES, DEFECTS AND LINE WIDTHS

The measurement system of the present invention is suitable for identifying and measuring a variety of features such as defects and line widths present on a photographic mask. A wide variety of defects may appear during the manufacture of the mask. FIGS. 3A through 3E illustrate examples of types of defects and a line width. Defects include isolated defects such as spots or holes, edge defects such as extensions and intrusions, and a wide variety of other types of defects. Other features that may be measured include the width of a chrome line or the width of spacing between such lines.

Figure 3A:
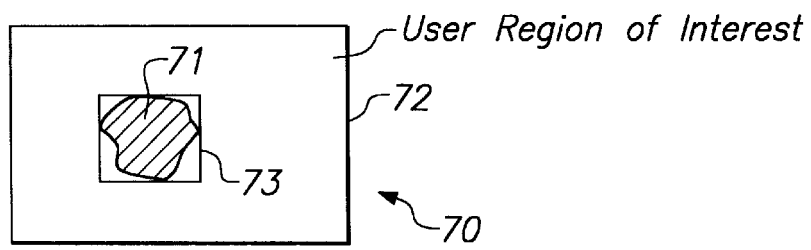
FIGS. 3A through 3E illustrate various features of a photographic mask each surrounded by a user region of interest.

FIG. 3A shows a feature site 70 to be measured. Feature site 70 includes a spot defect 71 surrounded generally by a user region of interest 72. A bounding box 73 bounds spot 71. A spot defect occurs when a particle of chrome or other contaminant is present by itself in location where it does not belong. As will be explained in greater detail below with reference to FIG. 4, when inspection machine 12 identifies a feature such as spot 71, the operator is able to enter review mode and to quickly surround spot 71 with a rough user region of interest 72 indicating the region that the user wishes to analyze and measure. Advantageously, the operator need only roughly draw a rough user region of interest around spot 71, and need not judge for himself the exact boundaries of the defect. Bounding box 73 is created by the measurement tool in order to determine the type of feature that the user has chosen to measure and will be explained in greater detail below with reference to FIG. 7B.

Figure 3B:
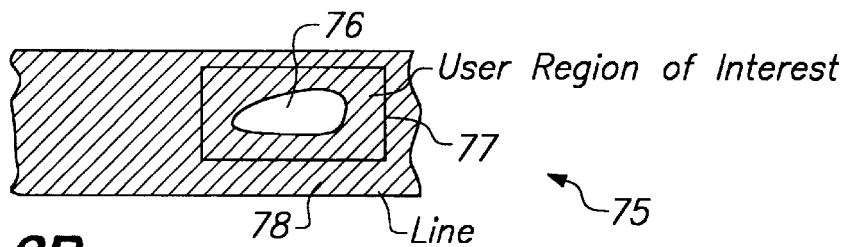
Figure 3C:
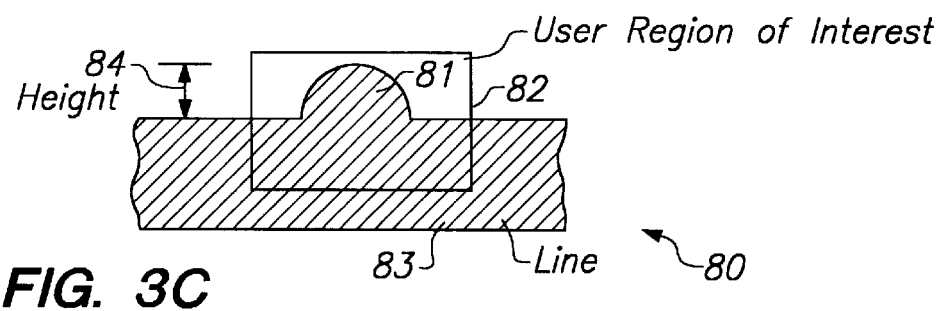
Figure 3D:
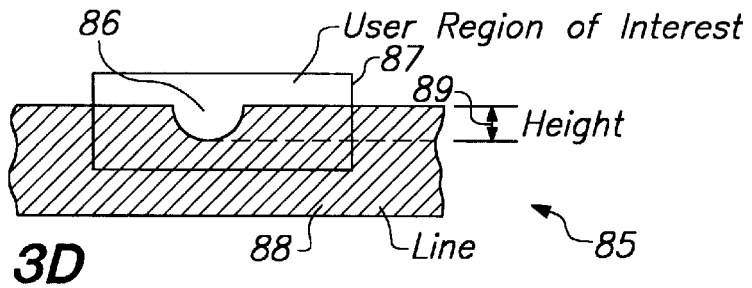

FIG. 3B shows a feature site 75 in which a line 78 has a hole defect 76. Hole 76 is surrounded by a user region of interest 77. A hole may occur when a section of a chrome line (for example) is lacking a piece of chrome such that a hole appears. FIG. 3C shows a feature site 80 in which a line 83 has an extension edge defect 81. This defect is surrounded by a user region of interest 82. An extension edge defect occurs when a portion of a line extends, or bulges out away from the line and is convex in shape. By convention, the height 84 of the extension refers to how far the defect extends from line 83. FIG. 3D shows a feature site 85 in which a line 88 has an intrusion edge defect 86. This defect is surrounded by a user region of interest 87. An intrusion edge defect occurs when a portion of a line is missing along an edge and has a concave shape. By convention, the height 89 of the intrusion refers to how far the defect intrudes into line 88.

Figure 3E:
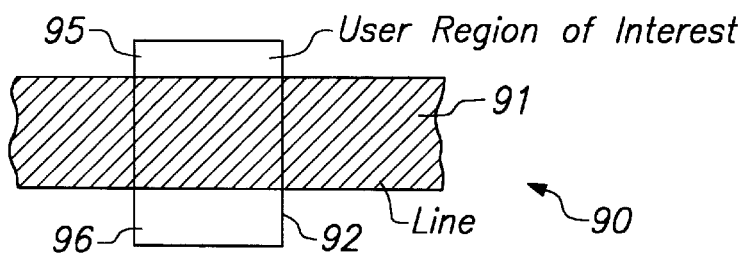

FIG. 3E shows a feature site 90 in which the width of line 91 is desired to be measured. A user region of interest 92 encompasses the width of line 91. Line 91 may be an opaque line, a transmissive clear region between lines, or other. As will be explained in greater detail below with reference to FIG. 7B, line 91 presents a dark region surrounded on either side by bright regions 95 and 96. With each of these defects and features, the operator is able to easily and quickly draw a user region of interest around the feature site to be measured and need not exercise any judgement regarding the size of the feature.

A wide variety of other types of defects and features such as dots, protrusions, corner defects, bridges, truncations, misplacements, half-tones, etc., as described in "SEMI Standards Programmed Defect Masks and Its Applications for Defect Inspection", by H. Kawahira and Y. Suzuki, SEMI Japan Standards Committee, Mountain View, Calif., may be analyzed and measured using the invention disclosed herein.

CALIBRATION CURVES

Figure 4:
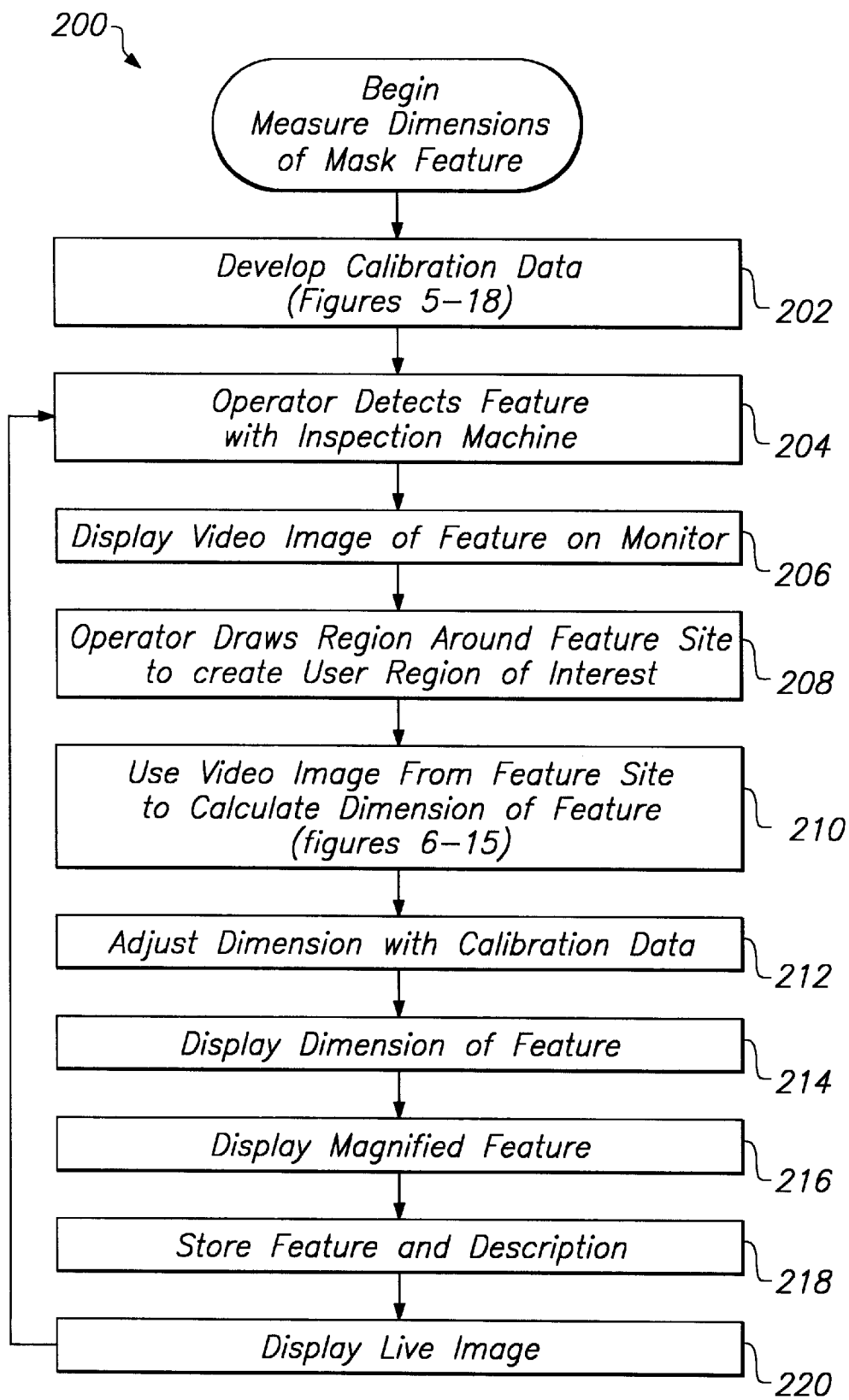
FIG. 4 is a flowchart for developing calibration data and measuring the dimensions a feature of a photographic mask according to one embodiment.

Now having described examples of various of the types of defects and features that may be measured using the present invention, a technique 200 for measuring various dimensions of these features is shown in FIG. 4. In one embodiment of the invention, an operator uses the inspection machine of FIG. 1 to inspect a photomask and identify features. Once a feature is found, the operator is then able to measure in-place a dimension of the feature using a connected computer which receives live video information from the inspection machine. Thus, analysis and measurement of the feature occurs while the mask is in place in the inspection machine and there is no need to remove the mask to another machine for measurement of a feature. This technique allows for extremely rapid measurements to be made. Measurements may be made of features of known sizes for producing calibration data, or of features of unknown sizes in a production environment.

In step 202, calibration data is developed using features of known sizes (such as from a VERIMASK) on the inspection machine that will be used to measure the actual defects. The calibration data is used to correct for non-linearities in the relationship between measured sizes and actual sizes. The operator interacts with the inspection machine to develop the calibration data preferably using a sequence of steps similar to steps 204–208, although any other suitable technique may be used in order to develop the calibration data. This step will be explained in greater detail below with reference to FIGS. 5–15.

Once the calibration data has been obtained for any number of feature types, this data is stored in the calibration database 54 of FIG. 2 and may appear in graph form as shown in any of FIGS. 16–18. These graph figures will now be explained before returning to step 204 of FIG. 4.

FIGS. 16A–16D and FIGS. 17A–17D show calibration plots for each of specific types of defects, while FIGS. 18A–18D show calibration plots for specific types of lines. Each of the graphs has for a vertical axis a measured value for the diameter (or width) of the feature in pixels. Each horizontal axis is the true reference diameter (or width) of the feature in microns as determined from an AFM measurement, a Vickers measurement, or other standard. Both the AFM measurement and the Vickers measurement are performed on very expensive, slow microscopes that are not suitable for production purposes but are extremely accurate. An objective absolute standard for obtaining reference measurements would be an NIST version of a VERIMASK plate. Other dimensions could be represented in these calibration plots such as feature area, height, etc.

Figure 16B:
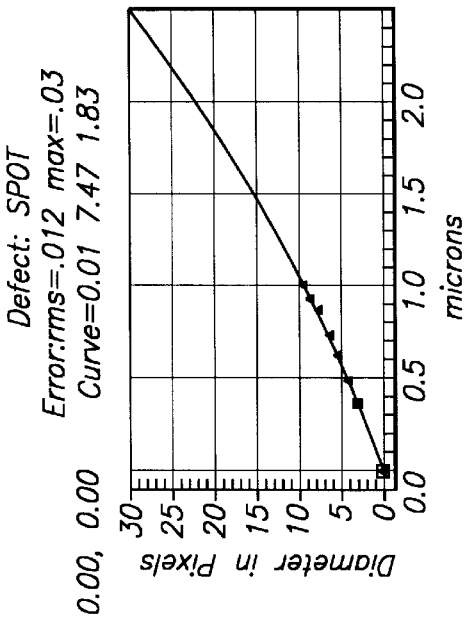
FIGS. 16A through 16D are calibration graphs for particular types of defects from which a reference measurement was obtained using an atomic force microscope (AFM).
Figure 16D:
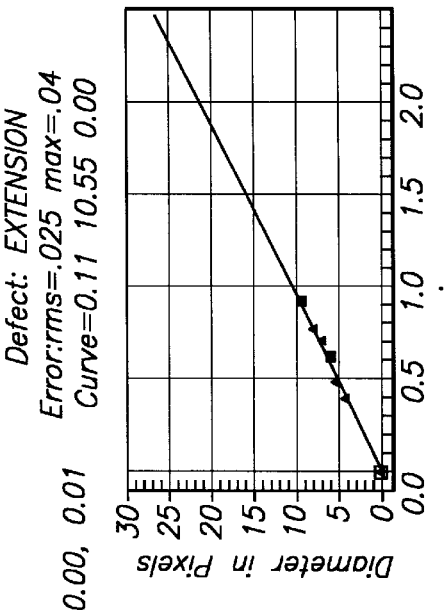
Figure 16A:
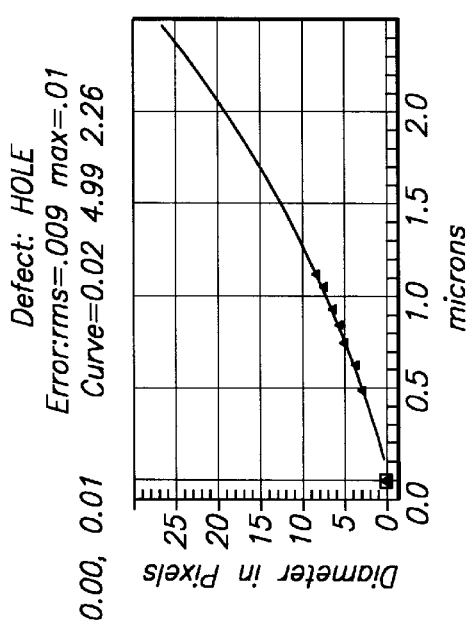
Figure 16C:
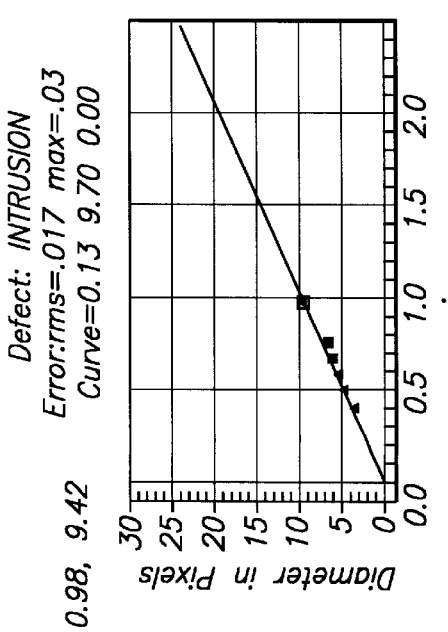
Figure 17A:
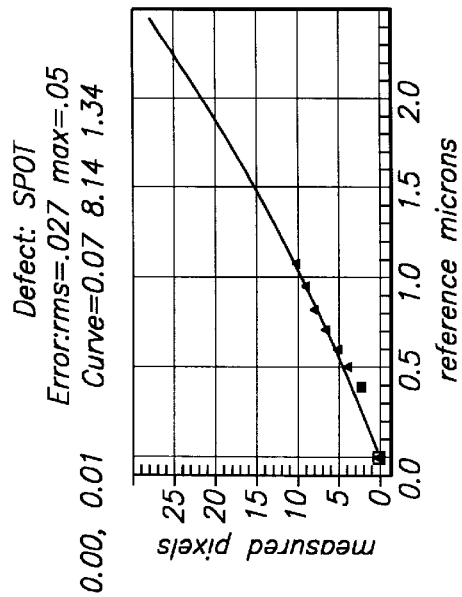
FIGS. 17A through 17D are calibration graphs for different types of defects from which a reference measurement was obtained using a Vickers machine.
Figure 17B:
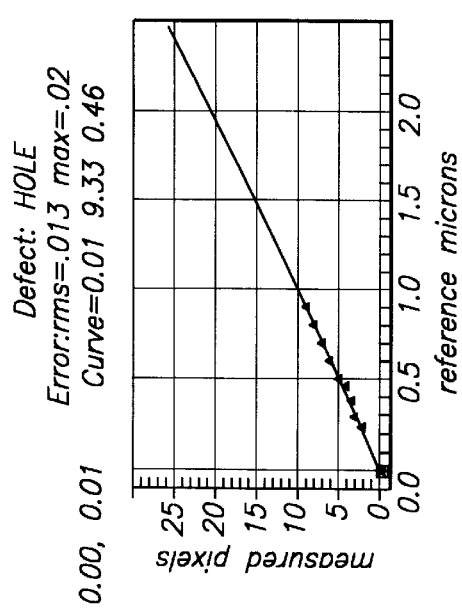
Figure 17C:
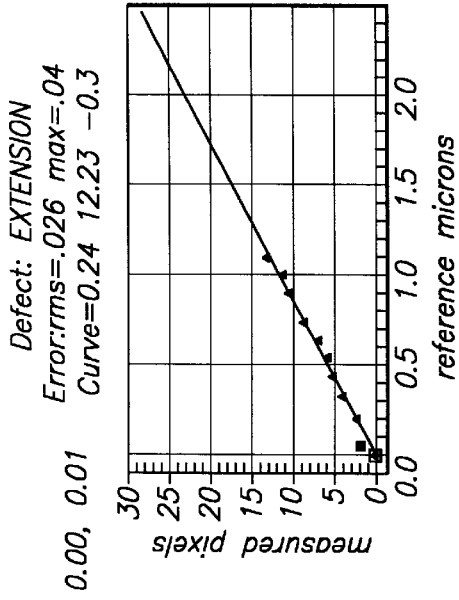
Figure 17D:
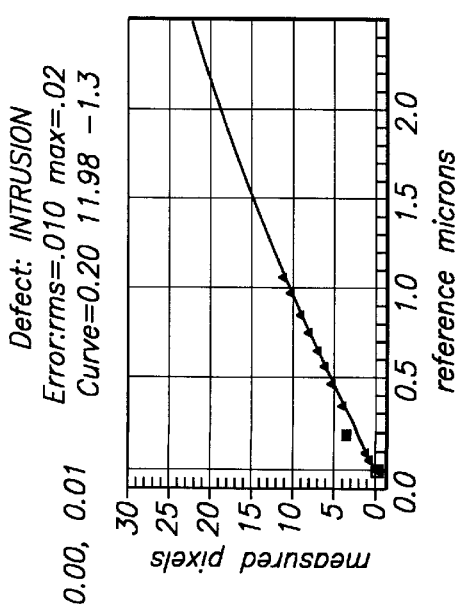
Figure 18A:
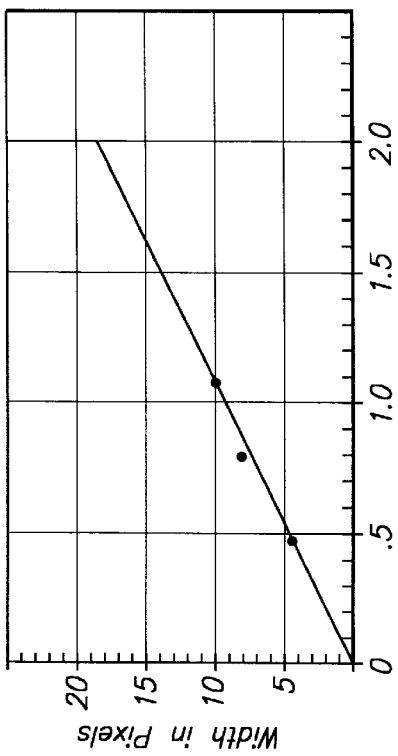
FIGS. 18A through 18D are example calibration graphs for different types of line widths as they may appear once a reference measurement is obtained.
Figure 18B:
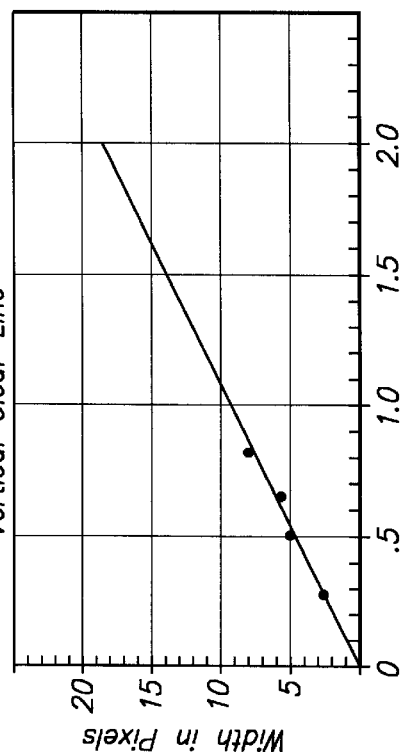
Figure 18C:
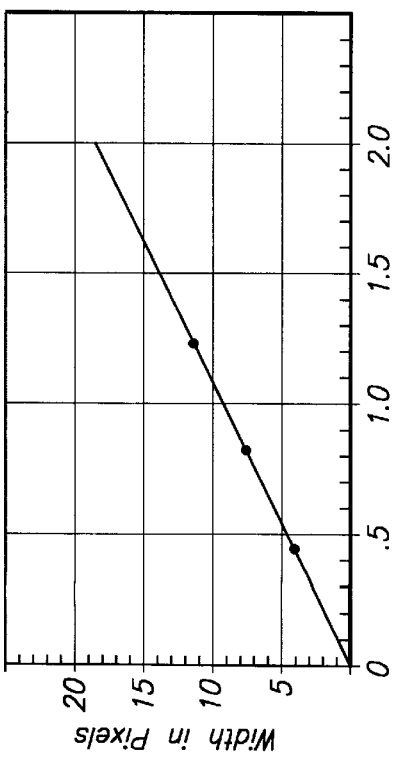
Figure 18D:
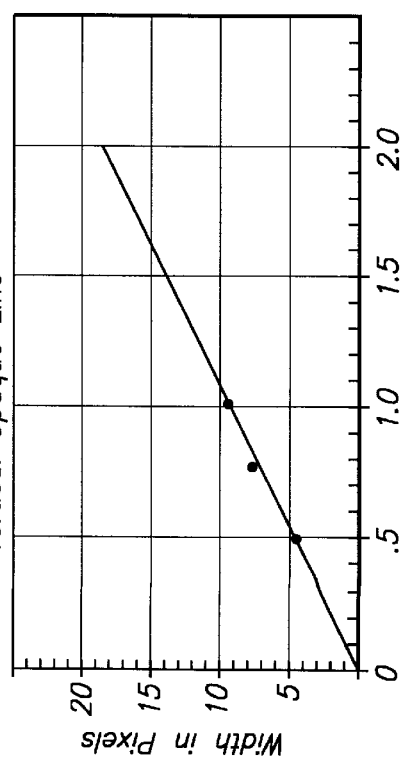

FIGS. 16A–16D and 17A–17D show respectively calibration curves for the defects hole, spot, intrusion and extension. FIGS. 16A–16B use a reference micron measurement from an AFM machine, while FIGS. 17A–17D use a reference micron measurement from a Vickers machine. FIGS. 18A–18D are possible calibration plots for line widths of horizontal opaque lines, horizontal clear lines, vertical opaque lines and vertical clear lines, respectively, and are illustrative of possible results for measuring line widths using any suitable reference measurement machine such as an AFM or Vickers.

For each feature type (hole, spot, etc.), the measurement tool is used to measure a number of features of different known sizes of that feature type using a known standard such as a VERIMASK in order to develop data points and a calibration curve such as those seen in FIGS. 16, 17 and 18. Because measurements of different features yield different results due to the inherent nature of the feature, having individual plots for each feature is advantageous in that more accurate measurements can be made for the actual features of that feature type. For example, referring to FIG. 16A, a measured hole defect having a diameter in pixels of twenty has a true size of 2.1 microns. And with reference to FIG. 16B, measurement of a spot defect having a diameter of twenty pixels results in a true size of 1.8 microns. Thus, it can be seen that for a measured value of twenty pixels for a defect, there is a difference of 0.3 microns in size depending upon whether the defect is a hole or a spot. Thus, development of calibration curves for each defect or line width is advantageous in that it results in greater accuracy for a measurement.

Additionally, separate calibration data for individual features can be developed for each objective of an inspection machine. Different objectives may have different characteristics affecting feature measurement. Also, the presence or absence of the compensation glass in an inspection machine (as required with through-the-pellicle KLA inspection) may cause different measurement results. Separate calibration data for individual features can also be developed for these situations. In general, a calibration plot can be developed for any unique combination of hardware in an inspection machine in order to compensate for its characteristics.

DIMENSION MEASUREMENT HIGH LEVEL FLOW

Once calibration data has been developed for each type of feature (such as shown in the graphs of FIGS. 16, 17 and 18), the measurement tool is then ready to measure the dimensions of actual features. In step 204, the operator detects a feature such as a defect or line width using the inspection machine. In this step the inspection machine scans the mask and identifies a feature. The inspection machine may identify a feature automatically, or the operator may assist in the identification of the feature. This inspection of a photomask may occur in a mask shop before the mask is shipped out to a customer, or may also occur in a wafer fabrication shop when a mask is received. Once a feature is detected, the inspection machine enters review mode and in step 206 the video image of the feature site is displayed on the monitor of the computer.

Next, in step 208 the operator draws a region (or user region of interest) around the feature to be measured (such as shown in FIG. 3). A wide variety of techniques may be used by the operator to indicate a user region of interest around the feature. By way of example, the operator may use a mouse, track ball or other input device to drag a region around the feature. Advantageously, the operator is not required to exercise judgment in placing the region exactly around the feature, but is only required to roughly place a region around the general area of the feature to be measured. Thus, operator judgment does not effect the outcome of the measurement, because the measurement tool is adapted to automatically identify the type of feature within the feature site and measure its dimensions automatically and accurately without further operator intervention.

Once the feature has been surrounded with a user region of interest, in step 210 the video image from the feature site is used to calculate the desired dimension of the feature. Dimensions of the feature to be calculated may include its area, diameter, width, height, and other dimensions. In one preferred embodiment, the calculation of a dimension of an actual feature may take place in the same way as test features of known sizes are measured in step 202 in developing the calibration data. This calculation of a dimension of an actual feature may take place as described in FIGS. 6–15.

Once a dimension of a feature has been calculated, the dimension (such as the diameter) of a feature is adjusted in step 212 using the calibration data contained in the calibration database (and as shown in graph form in the examples of FIGS. 16–18). For example, referring now to FIG. 16A, if the diameter of a hole defect has been measured to be five pixels, then referring to the plot reveals that a diameter of five pixels is 0.7 microns in width. In this fashion, a measured dimension of a feature in pixels can be referenced to the calibration data in order to obtain an extremely accurate "true" value for the dimension of the feature in microns. This technique can be used for any dimensions such as area, width, height, etc. The creation of this calibration database which is represented graphically in the example plots of FIGS. 16, 17 and 18 will be explained in greater detail below with reference to FIG. 5.

Once the dimension (such as diameter, width, height, etc.) of the feature has been accurately determined, in step 214 the dimension of the feature in microns is displayed on the computer monitor. In step 216 the feature image is magnified and displayed with a one by one micron grid for a sanity check. In step 218, the operator has the option to store the feature and its measured dimensions along with a description into a feature database for later retrieval and analysis. The operator may also print images of the feature and its dimensions at this time. It should be noted that at any time in this process, previously stored features and dimensions may be reviewed, and these selected features and associated text can be selected and printed. Once the operator has finished with a particular feature, in step 220 the live image display is returned to the computer monitor and the operator continues to detect and measure additional features in step 204.

DEVELOPMENT OF CALIBRATION DATA

Figure 5:
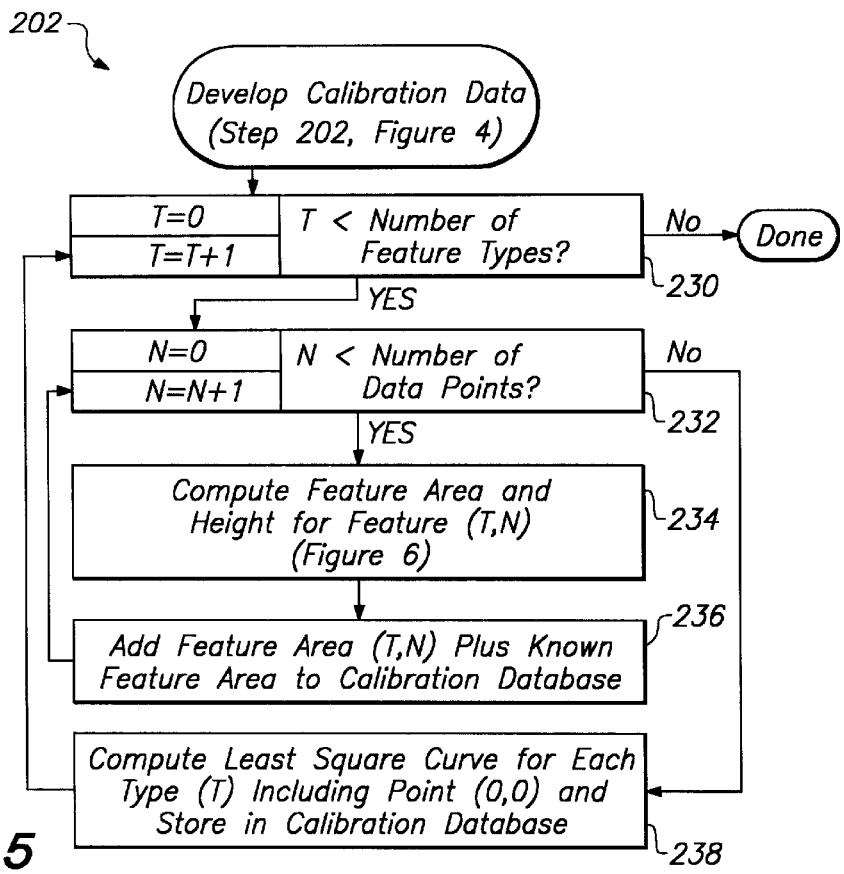
FIG. 5 is a flowchart for the develop calibration data step of FIG. 4.

FIG. 5 illustrates one embodiment of a technique for performing the develop calibration data step 202 of FIG. 4. This step is used to develop calibration data for each of a variety of feature types such as defects and lines. For each type of defect and/or lines, a number of different sizes for that particular defect or line width will be measured in order to produce a number of data points for producing a polynomial curve. A polynomial curve typically results from the plotting of data points for features less than 1 micron in size because these sizes are approaching the size of the light photons used to measure the feature. In other words, the relationship is non-linear and a polynomial curve results (often quadratic) because the features are so small that the size of the light photons (about 0.5 microns) used to measure the features starts to interfere with the measurement. A polynomial curve is advantageous when the size of features to be measured is less than twice the wavelength of the light used to illuminate and measure the feature. By way of example, for visible light, a polynomial curve is advantageous for features less than one micron in diameter.

For example, referring to the hole defect plot of FIG. 16A, it can be seen that seven different sizes of hole defects ranging from about 0.5 microns to 1.1 microns have been measured in order to develop a non-linear calibration curve for that type of defect. Thus, a measured value for an actual hole defect may reference this data to obtain a more accurate measurement.

Step 230 implements a loop through each type of feature and develops calibration data to produce a calibration plot for each feature type. In one embodiment, there are eight feature types that include the defects hole, spot, intrusion and extension, and line width features that include horizontal opaque lines, horizontal clear lines, vertical opaque lines, and vertical clear lines. Of course, calibration plots may be developed for other feature types. When all features have been analyzed and measured this step is done. Step 232 implements a loop that measures a variety of data points for each type of feature. For example, as shown in the hole defect plot of FIG. 16A, there are seven sizes of holes that are measured that produce seven data points for the plot resulting in a particular calibration curve for that type of defect. Any number of sizes of a feature type may be measured in this step. For each size of these artificial features, steps 234 and 236 are executed. Once each of the sizes has been measured, control moves to step 238.

In step 234 the feature area and height for a particular size of a particular feature type is computed. This step will be explained in greater detail below with reference to FIG. 6. Also, the line width may be calculated from the feature area because as seen in FIG. 10E, area 395 from profile 396 of line 392 when divided by the region of interest (ROI) height yields line width 394. Additionally, this step may also be used to calculate dimensions of an actual feature to be measured such as described in step 210 of FIG. 4.

In step 236 the computed feature area for the particular size of a particular feature is added to the calibration database along with the previously (or known) feature size. In this step, the measured height of the feature may also be added to the calibration database.

The calibration database may be implemented and organized in a wide variety of manners. By way of example, the calibration database contains a list of the measured feature area (or other dimension) for each defect size and its corresponding reference size in microns. The reference size in microns is known because the VERIMASK has artificially produced defects and line widths with known sizes that have been measured using an extremely accurate measurement device such as an atomic force microscope (AFM) or a Vickers machine. In step 236 when the measured feature area is added to the calibration database, the operator may be prompted to enter the reference size in microns, or the reference size in microns may be entered automatically along with the measured size in pixels by the computer. In one embodiment, a defect is assumed to be circular, the diameter of the defect is determined from the measured feature area and this diameter in pixels is entered into the calibration database along with its corresponding true diameter in reference microns. Such an entry in the calibration database represents one of the data points such as those shown in FIG. 16A or any of the other plots shown in FIGS. 16, 17 or 18. Once step 232 adds the data associated with one feature size, control returns to step 232.

Once step 232 has finished computing all of the data points for a particular feature type, control moves to step 238. In step 238, the data points developed for a particular feature type are used to produce a calibration curve such as those seen in FIGS. 16, 17 and 18. This calibration curve and its corresponding polynomial formula are then also stored within the calibration database for later reference in determining the actual size of an actual defect. In one embodiment of the invention, step 238 is performed by computing a least square curve for each feature type (including the data point 0,0). This curve and its corresponding polynomial formula (such as $ax^2+bx+c$) then stored in the calibration database. Once a calibration curve has been computed and stored in the calibration database for a particular type of feature, control returns to step 230 and calibration curves are developed for each of the remaining types of features. Once all of the calibration data has been obtained for each feature type, then the develop calibration data step is done.

PROFILE DEVELOPMENT, FLUX, AREA AND LINE MEASUREMENT

Figure 6:
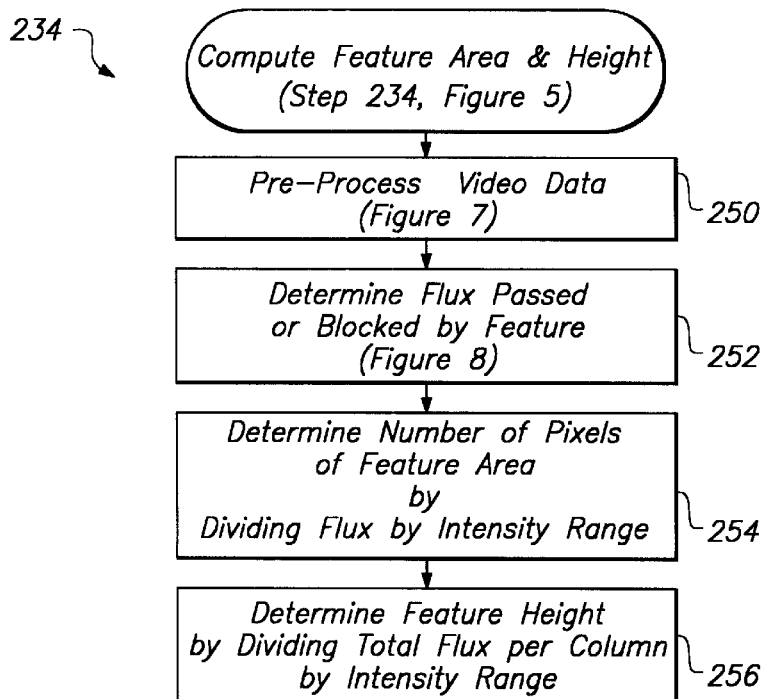
FIG. 6 is a flowchart for the compute feature area step of FIG. 5.

FIG. 6 illustrates one embodiment of a technique for computing the feature area and height, step 234 of FIG. 5. In step 250, the video data is pre-processed in order to determine an intensity range, determine the feature type, determine a size for system regions of interest around the feature and to produce a good quality flux source image from which the flux passing through the feature will be determined. The video data being processed may represent test data for a standard feature of a known size used for developing calibration data, or may represent video data of an actual feature to be measured. This step will be explained in greater detail below with reference to FIG. 7.

Once the video data has been pre-processed and a good quality flux source image produced, in step 252 the flux that is passed or blocked by the feature is determined. This step develops multiple profiles of a particular feature and chooses the best profile in order to determine the flux. Flux corresponds to the number of light photons passing through a medium and is expressed in units of scaled photons. An opaque feature such as a spot or a line blocks the passage of photons and reduces flux, while a clear portion of a mask such as formed by the space between lines, or the gap created by an intrusion into a line, passes photons easily and results in an increase in flux. This step will be explained in greater detail below with reference to FIG. 8.

Once the flux has been determined, in step 254 the number of pixels of the feature area is determined by dividing the determined flux by the intensity range. In this fashion, the feature area in pixels can be determined and the diameter of the defect or the width of the line can be easily determined from the feature area. For example, the line width dimension may be calculated from the feature area because as seen in FIG. 10E, area 395 from profile 396 of line 392 when divided by the region of interest (ROI) height yields line width 394. Because flux is measured in photons, and the intensity range is measured in photons/square pixel, the division of flux by intensity range gives an area in square pixels which yields a diameter or width. This measured diameter or width in pixels can then be added to the calibration database along with the reference feature dimension (if calibration data is being developed), or the diameter or width in pixels can be referenced to one of the calibration plots in order to return a true size in microns (if an actual defect or line width is being measured).

In step 256 the total flux determined from one column of the intensity profile can be used to determine the height of a defect or line by dividing the total flux by the intensity range. This height in pixels can then be added to the calibration database (for test features) or may be referenced to a calibration plot for determining an accurate height of actual features. Determining height is advantageous for evaluating how far edge defects extend from, or intrude into a line.

Figure 7:
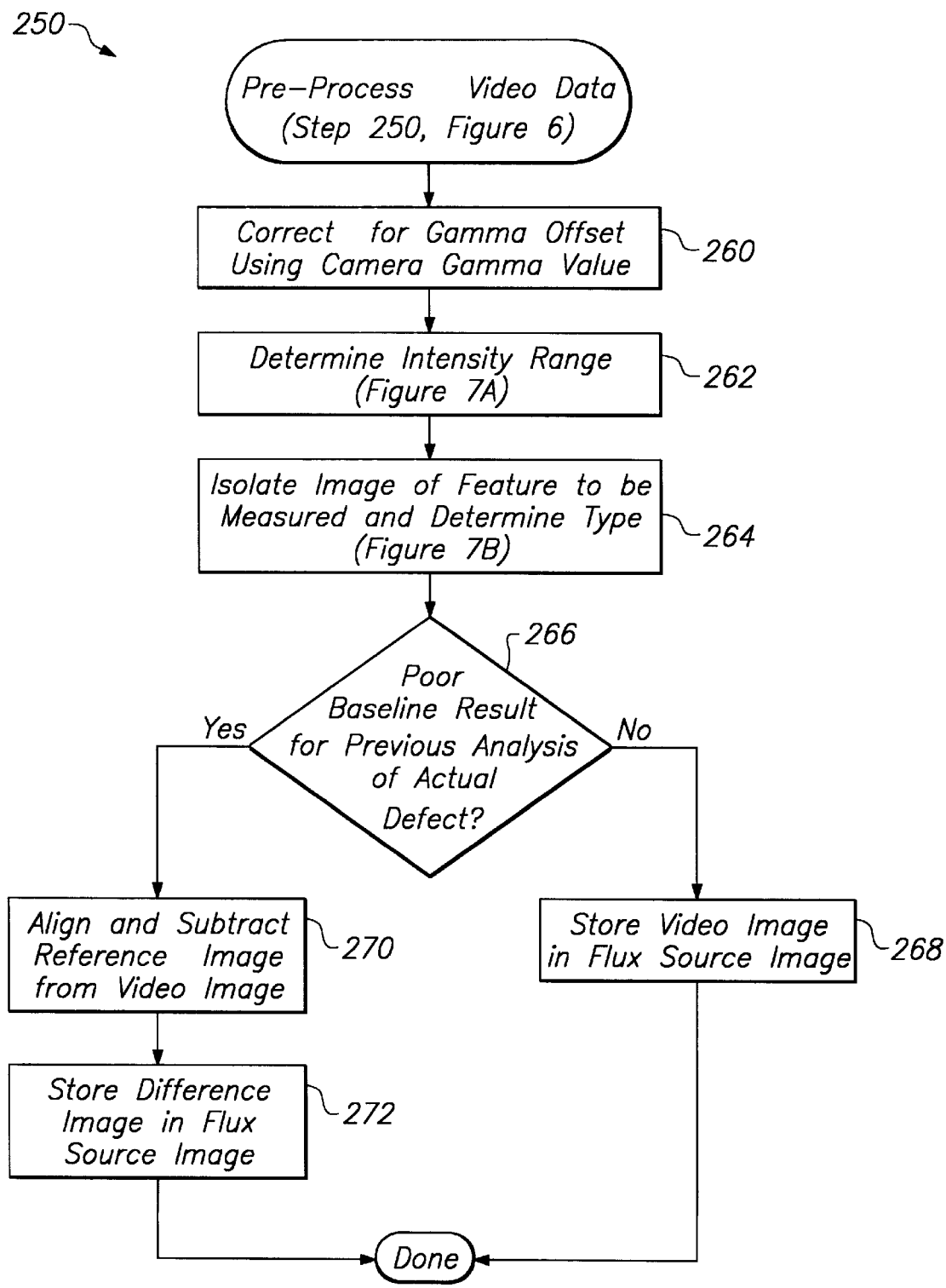
FIG. 7 is a flowchart for the pre-process video data step of FIG. 6.

FIG. 7 illustrates an embodiment of the pre-process video data step of FIG. 6. This step is used to determine the intensity range for the feature, determine the type of the feature, to obtain a reference image if needed, and to produce a good quality flux source image. In step 260 the camera gamma value is used to correct for the gamma offset of the camera optics. A camera gamma value is intrinsic to all camera electronics and has a known value for each camera. Because the light input to the camera versus the voltage output is non-linear, it is corrected for in this step.

In step 262 the intensity range for the feature to be measured is determined. An intensity value or range may be determined in a wide variety of manners. By way of example, step 262 presents one possible technique. The value for intensity range represents a range from the dark peak mean to the bright peak mean and is constant for changes in illumination or camera gain. Intensity range is expressed in digitized units (representing photons/square pixel), ranging typically from 0 to 255 for a gray scale image. A "0" value represents one end of the spectrum such as chrome being present, and a "255" value represents the other end such as a clear portion of the mask. Generally, a value of 255 for intensity is equivalent to about 10,000 photons. This step will be explained in greater detail below with reference to FIG. 7A.

In step 264 the feature to be measured is isolated and its type is determined. A bounding box is used to surround the feature and to determine its type. This step will be explained in greater detail below with reference to FIG. 7B.

Figure 13:
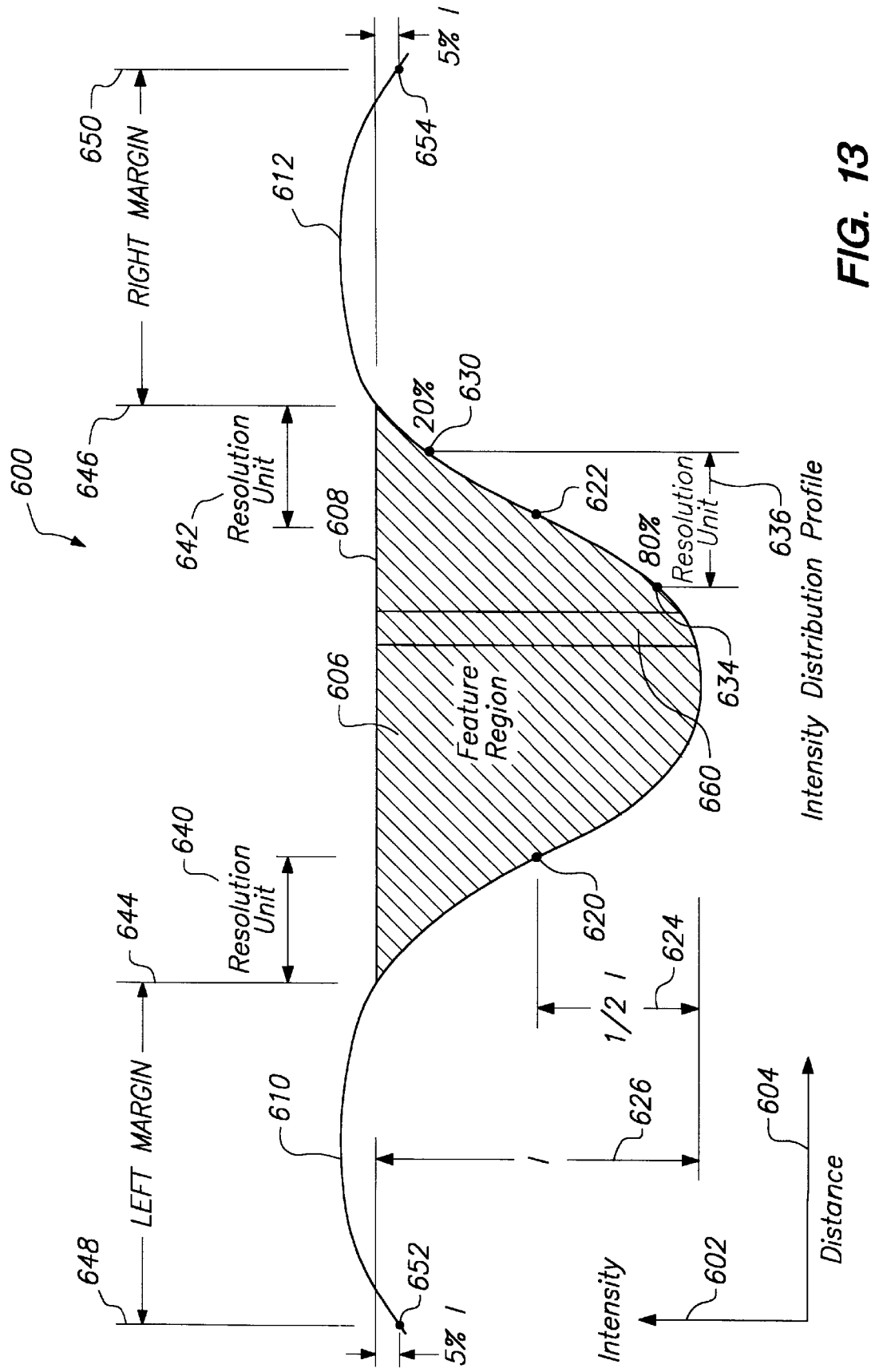
FIG. 13 illustrates in greater detail the intensity distribution profile of FIG. 11A.

The following steps 266–272 ensure that a good quality flux source image is available for producing a good profile. The development and use of profiles in determining flux will be explained in greater detail below with reference to FIG. 8. Actual features to be measured often end up producing a low quality profile having a poor baseline (jagged, uneven, or non-linear) because the feature may be fairly complex. For example, a defect such as an edge defect may be located on a curve of a line rather than on a straight edge, and isolated defects may be located extremely close to other features which effect the developed profile for that feature. Thus, for actual features measured, if a good profile can not be obtained, it may be necessary to obtain a reference image for that feature. FIG. 13 is an example of a profile having a good baseline, i.e., the baseline is fairly linear and the standard deviations of its left and right margins are fairly low.

If a profile has been developed for an actual feature (as will be discussed in FIG. 8), and that profile has a baseline that is not straight, then steps 270 and 272 are performed in order to obtain a good quality flux source image. In step 270 the operator is prompted to obtain the reference image for the feature site under consideration and this reference image is then subtracted from the current actual feature site which contains the defect. A reference image is a good image of the mask as it should appear without a defect. This reference image may be obtained from a mask database, or from a mask on a previous die. By subtracting the reference image from the actual image, any complex features surrounding the feature to be measured are removed from the image and only the defect to be measured remains in the image. Next, in step 272 this difference image is stored as the flux source image.

On the other hand, artificial defects and most of the actual features are treated differently. Because a standard, artificial defect used for calibration purposes is very simple and not complex, such a feature usually always has a good profile with a straight baseline. Thus, for calibration features, the result of step 266 is no, and in step 268 the current video image is stored as the flux source image. Also, for the measurement of actual features, the first time the feature is measured there is no profile developed at this point in time so the video image for that feature will also be stored as the flux source image in step 268. Additionally, for measurement of line widths, a good profile is usually obtained so step 268 is performed. Once a video image has been stored as the flux source image (in either steps 268 or 272), the measurement tool is ready to determine the flux passed or blocked by the feature by referring to the flux source image.

FIG. 7A illustrates one technique for determining the intensity range, step 262 of FIG. 7. The intensity range is used along with the flux determined in order to determine the number of pixels in the feature area. A value for the intensity range is used instead of just an intensity value to compensate for light changes affecting the flux value. For example, if the camera gain doubles or more illumination is used on a feature then the flux would double and affect the measurement of the feature dimension. But if the illumination doubles, the intensity range would also double and a measurement would stay constant.

In step 274 an intensity histogram for the feature is computed. A histogram is a plot of light intensity values versus areas occupied by each intensity value and is used in order to determine the intensity range for the feature site. FIG. 9 illustrates an example of a histogram 300 that may be used to determine the intensity range of a particular feature. This histogram example has an intensity axis 302 ranging from 0 to 255 and an area axis 304 representing the area in pixels that a particular intensity occupies. This example feature has a histogram 306 defining dark intensity areas 308, bright intensity areas 310, and intermediate gray intensity areas 312. The top of the dark area yields a dark peak mean 314 and the top of the bright area yields a bright peak mean at 316. Using the computed histogram for this feature, in step 276 the dark peak mean intensity and the bright peak mean intensity are determined by reference to the dark peak mean 314 and the bright peak mean 316 of the computed histogram. The intensity range is then determined by subtracting the dark peak mean intensity from the bright peak mean intensity. Thus, were illumination to double, the peaks would be twice as far apart and the intensity range would also double and a measured feature area would remain constant.

Step 278 determines whether a good histogram has been obtained by determining whether one of the peaks is missing. A good histogram will typically have a dark peak that is four times greater in area than the valley of the gray region 312 and a bright peak that is four times greater in area than the valley region. If a good histogram cannot be obtained by analyzing a small region around the defect, then a larger region around the defect is analyzed. For isolated defects, such as spots or holes, there will either be all black or all white around the defect, so it makes no difference how big the analyzed image is. If a good histogram cannot be obtained by analyzing a larger region around the defect, then in step 280 the histogram value from the best recent good image is used.

Figure 7B:
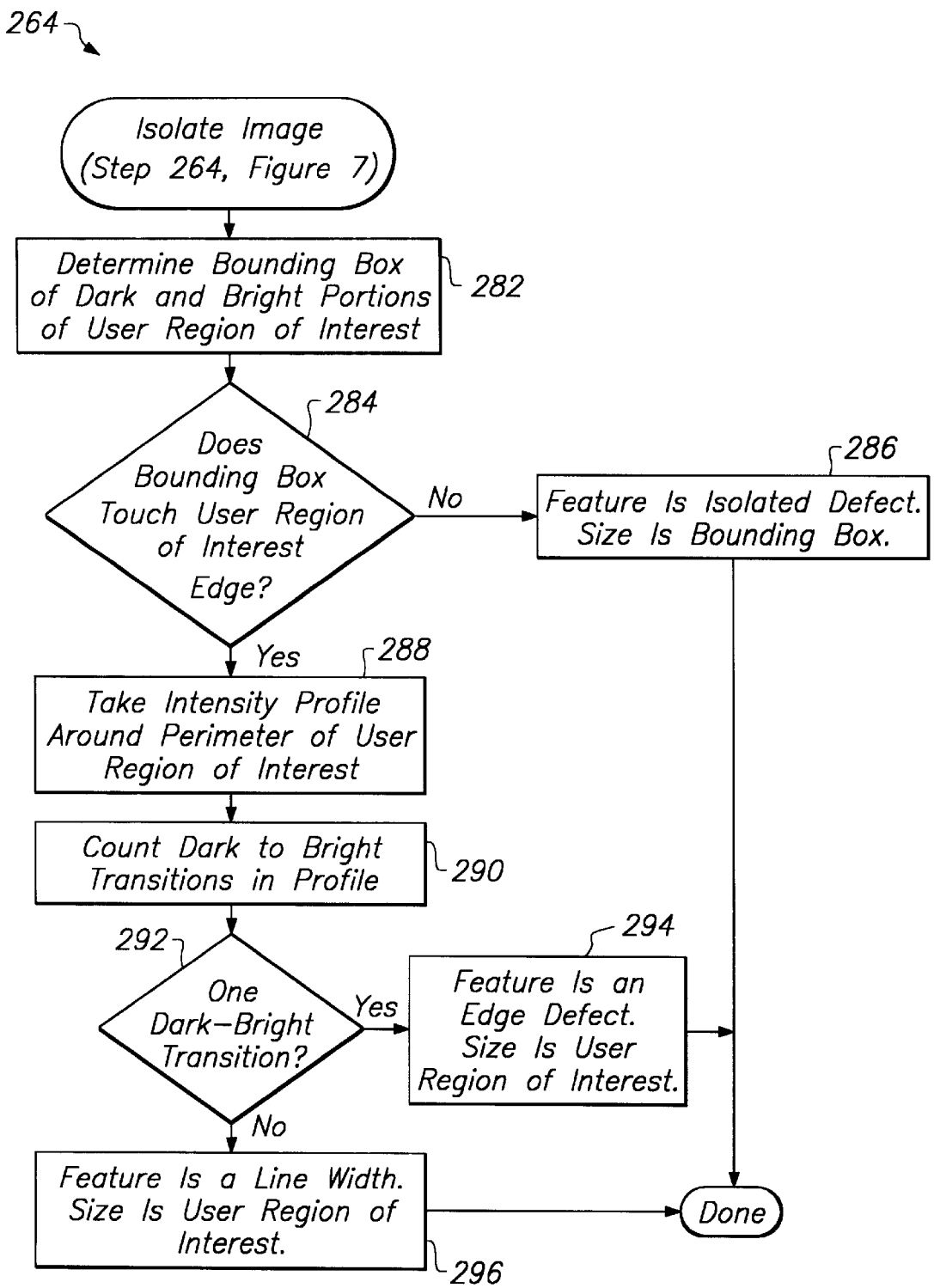
FIG. 7B is a flowchart for the isolate image and determine feature step of FIG. 7.

FIG. 7B illustrates a technique for isolating the image of the feature to be measured and for determining its type, step 264 of FIG. 7. This step returns a size for the system regions of interest used in developing profiles of FIG. 8 and also determines the type of the feature. In step 282, bounding boxes are determined for the dark and bright portions within the video image of the user region of interest. A bounding box determines the extent of contiguous dark or bright features. Determining bounding boxes may be done in a wide variety of manners. By way of example, the technique known as "blob analysis" may be used to determine the bounding boxes.

For example, feature site 70 of FIG. 3A shows a spot defect 71 surrounded by a bounding box 73. This bounding box 73 tightly conforms to the outline of spot 71 and is completely contained within user region of interest 72. A bounding box for hole 76 of FIG. 3B would similarly tightly surround the hole and would be contained completely within the user region of interest. By contrast, bounding boxes formed for other features such as the extension, intrusion and line of FIGS. 3C, 3D and 3E would not be completely contained with the user region of interest but would be collinear with the identified user region of interest. Bounding boxes for these features touch the user region of interest because the dark and bright areas of the feature are not completely isolated within the user region of interest but extend to the border of the user region of interest.

In this way, an analysis of the bounding boxes formed can help determine the type of the feature. In step 284 it is determined if the bounding box for a dark or bright feature touches the edge of the user region of interest. If the answer is no, then in step 286 it is determined that the feature is an isolated defect such as a spot or a hole, and the size used to help determine the size of system regions of interest is determined to be the size of the bounding box.

However, if the bounding box does touch the user region of interest, then the feature may be an edge defect or a line width. Thus, in step 288 an intensity profile is taken around the perimeter of the user region of interest. Because the user region of interest may be asymmetrical, it is advantageous to take the profile around the perimeter, although in an ideal situation a portion of the perimeter may be used. This intensity profile will identify dark and bright areas and transitions in-between. In step 290 the number of dark to bright (or bright to dark) transitions in the intensity profile are counted. An example of the use of counting such dark to bright transitions may be seen in the examples of FIGS. 3D and 3E. For example, in FIG. 3D the edge defect within the user region of interest has only one bright area outside the line and the one dark area being the line itself. Therefore, there is only one dark to bright transition from the line to the area outside the line. By contrast, FIG. 3E shows how bright regions 95 and 96 are outside of the dark line region 91. Thus, there are two dark to bright transitions, one on each side of line 91.

The number of dark to bright transitions may then be used to determine the type of feature. Step 292 tests whether there is one dark to bright transition. If so, then in step 294 it is determined that the feature is an edge defect and the size used to help determine the size of system regions of interest is determined to be the complete user region of interest. However, if there is more than one dark to bright transition, then step 296 determines that the feature is not a defect but is a line width, and the size used to help determine the size of system regions of interest is determined to be the user region of interest. After steps 286, 294 and 296 have completed, step 264 of FIG. 7 is done.

Once the pre-processing of the video data has determined the intensity range for the feature, has determined the type of the feature and has returned a size for system regions of interest, FIG. 8 provides a technique by which the flux that is passed or blocked by the feature in the video image is determined, step 252 of FIG. 6. Once the flux is determined, then the area of the feature may be calculated. FIG. 8 illustrates a technique by which multiple regions of interest (system regions, as opposed to the original user region of interest) are each used to create a profile for the feature to be measured. These profiles are then analyzed to determine which profile provides the best flux measurement for the feature to be measured. Through the use of this technique, edge defects that lie along an edge angled off of the horizontal may be measured accurately, as well as line widths for lines that are not horizontal.

In step 400 multiple system regions of interest for a particular feature to be measured are produced depending upon whether the feature is a defect or a line width. These multiple regions of interest are additional regions of interest developed by the measurement tool and are distinct from the original user region of interest that the operator specifies in identifying a feature. This step will be discussed in greater detail below with reference to FIG. 8A. Next, in step 402 a profile is developed for each of the regions of interest produced in step 400 and is discussed in greater detail below with reference to FIG. 8B. In step 404 profile statistics are developed for each profile in order to determine which profile provides the best flux measurement and is discussed in greater detail below with reference to FIG. 8C. In step 406 the profile statistics for each of the profiles is used to determine which profile provides the best flux measurement for the feature of interest, and is discussed in greater detail below with reference to FIG. 8D. The best flux measurement is then used as the determined flux value for step 252 of FIG. 6.

Figure 8A:
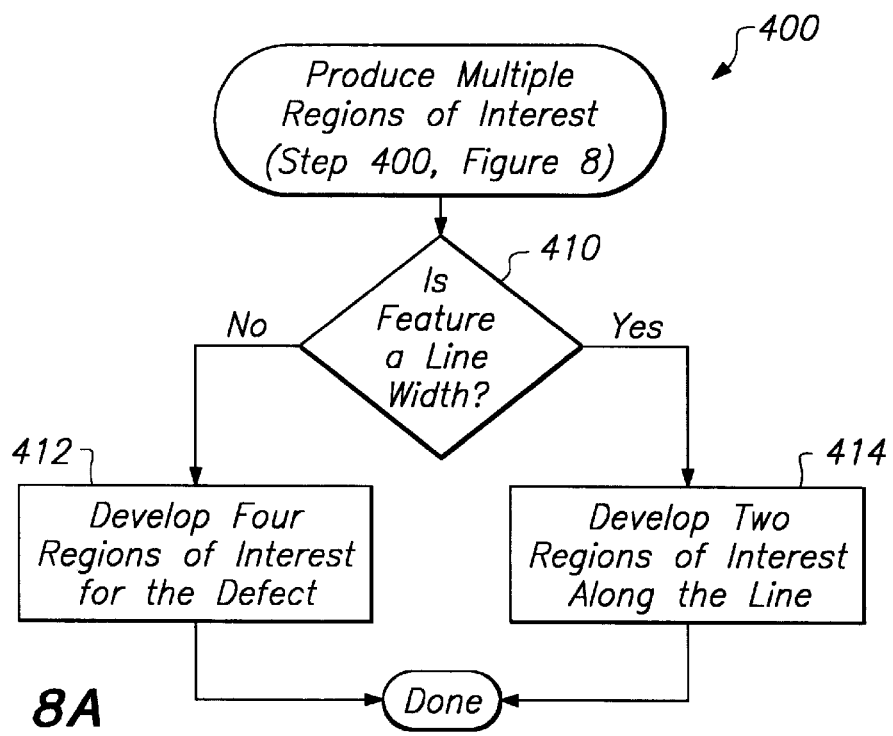
FIG. 8A is a flowchart for the produce multiple regions step of FIG. 8.

FIG. 8A illustrates one embodiment of a technique for producing multiple regions of interest, step 400 of FIG. 8. Step 410 tests whether the feature is a line width or a defect, the type of feature already having been determined above in FIG. 7B. If the feature is an isolated or edge defect, then in step 412 four system regions of interest are developed for the defect.

Examples of four possible system regions of interest developed for a spot defect (for example) are shown in FIGS. 10A–10D. FIG. 10A shows a vertical region of interest 350 surrounding a spot defect 352. FIG. 10B shows a horizontal region of interest 360 surrounding a spot defect 362, and FIGS. 10C and 10D show angled regions of interest 370 and 380 surrounding the spot defects 372 and 382 respectively. Of course, many other orientations for the multiple regions are possible.

Multiple regions of interest are useful for producing a good profile of the defect. If the defect is on an edge, then a profile is best taken parallel to the edge in order to obtain a good profile with a straight baseline. Also, if the defect is near or on a diagonal line, then the profile should be taken on the diagonal that is parallel to the diagonal line. And because these edges or lines may be horizontal, vertical, or at a 45 degree angle, multiple regions of interest that run parallel to these edges are useful. Most lines and edges on a photomask are horizontal or vertical, but some are at a 45 degree angle.

Because of feature crowding on a photomask (due to the ever decreasing size of the mask and its features), isolated defects may also often be found on or near a horizontal, vertical or diagonal line. Also, it is likely that a defect may be found on an edge. Thus, the development of multiple regions of interest ensure that at least one of the multiple regions of interest will enable a profile to be taken parallel to an edge near the defect.

Height 391 and width 393 conventions for system regions of interest are shown in FIG. 10E. The size and angle of each of the system regions of interest developed in step 412 for a defect may be determined in a wide variety of manners. By way of example, the width may be determined by multiplying the Blur Size by four, and the height may be determined by adding the Blur Size to a user defined height or to the size determined in FIG. 7B. The user defined height can be pre-programmed or chosen by the user from the computer. The angle for the regions of interest in FIGS. 10C and 10D may be any angle; a 45 degree angle works well.

The Blur Size is an empirically determined value in pixels that is an estimate of the resolution unit for the optics used; calculation of its value will be explained in greater detail below with reference to FIG. 13. It should be appreciated that any number of regions of interest may be developed, although developing fewer regions of interest may result in a poor profile being developed, leading to an inadequate measurement of the feature area. Once these multiple regions of interest have been developed in step 412, then step 400 is done.

Returning now to step 410, if the feature is determined to be a line width, then in step 414 two regions of interest are developed along the line to be measured. Examples of two regions of interest 396 and 398 are shown in FIG. 10E. These two regions of interest are developed along line 392 having a width 394. Two regions of interest are used to help determine the flux through a line because the line may be slightly angled. By providing two parallel regions of interest 396 and 398, the angle of the line can be corrected for as will be explained in greater detail below with reference to FIG. 8D. The height 391 and width 393 of these two regions of interest may be any suitable value. By way of example, a width equal to a user defined height (or the size determined in FIG. 7B) plus twice the Blur Size works well. A height equal to seven pixels also works well. Once these two regions have been developed in step 414 then step 400 is done.

Figure 8B:
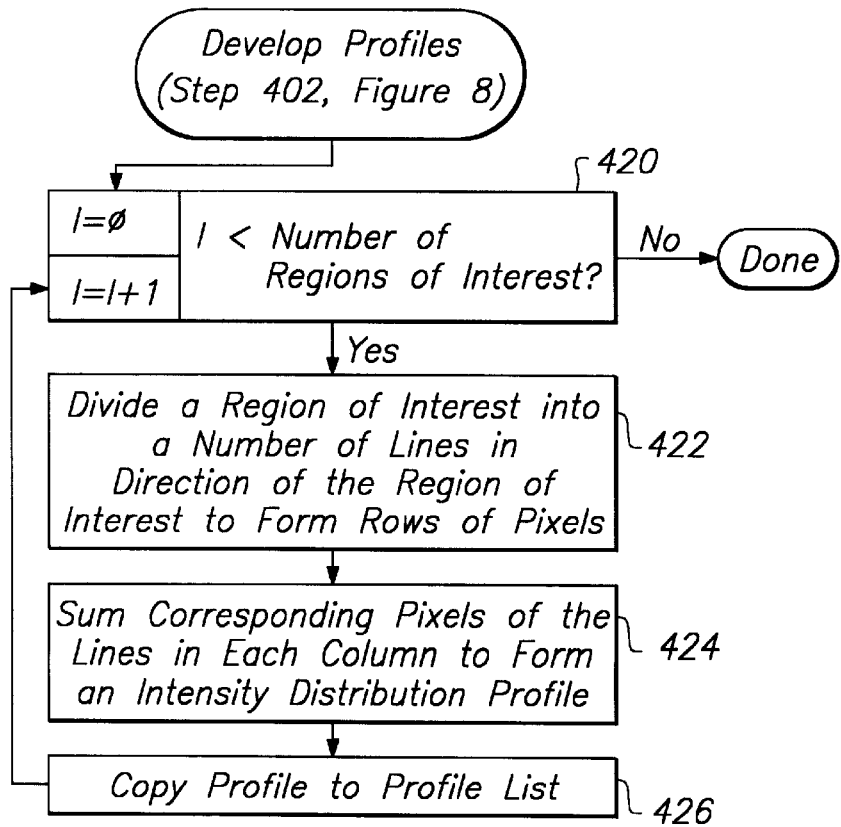
FIG. 8B is a flowchart for the develop profiles step of FIG. 8.

After the multiple regions of interest are produced, then in FIG. 8B a technique is shown for developing an intensity distribution profile for each of the produced system regions of interest. This technique will be explained with reference to FIGS. 11 and 12. Step 420 of FIG. 8B loops through steps 422–426 for each of the multiple regions of interest produced in step 400 of FIG. 8. Once a profile has been developed for each region of interest then step 402 is done.

Figure 11A:
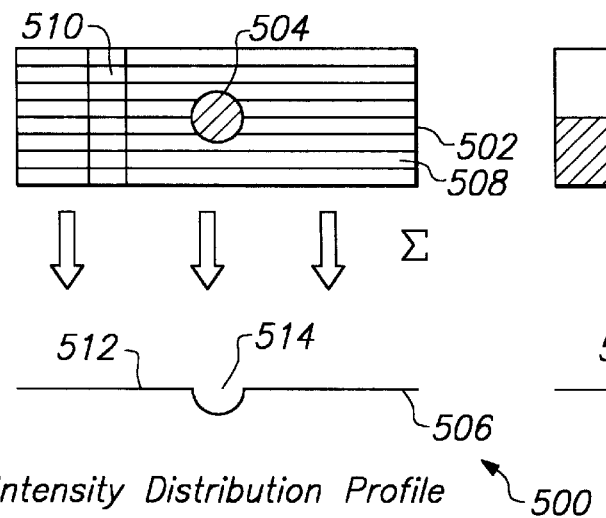
FIGS. 11A through 11C illustrate how a system region of interest of a flux source image may be summed in order to create an intensity distribution profile for a particular feature.

In step 422 one of the multiple regions of interest is divided into a number of lines in the direction of the region of interest in order to form rows of pixels. This step is illustrated in FIG. 11A, for example. FIG. 11A shows a process 500 in which a region of interest 502 surrounding a spot defect 504 is used to develop a profile 506. Because region of interest 502 derives from a video image of the feature site, it is composed of pixels. This step divides the region of interest into rows of pixels 508 along the direction of the region of interest, which in this case happens to be horizontal. A region of interest that was angled would be divided into rows of pixels that are parallel to its length.

Next, in step 424 corresponding pixels in the rows of pixels 508 are summed in each column in order to form an intensity distribution profile 506. As shown in FIG. 11A, a column of pixels 510 is summed in order to form a portion of the profile 506. Using this technique, profile 506 has a flat baseline 512 except in the location of the spot defect 504 which is where a dip in the intensity of the profile 514 is caused by spot defect 504. The intensity dips at this point because spot defect 504 prevents flux from passing through the stop.

Figure 11B:
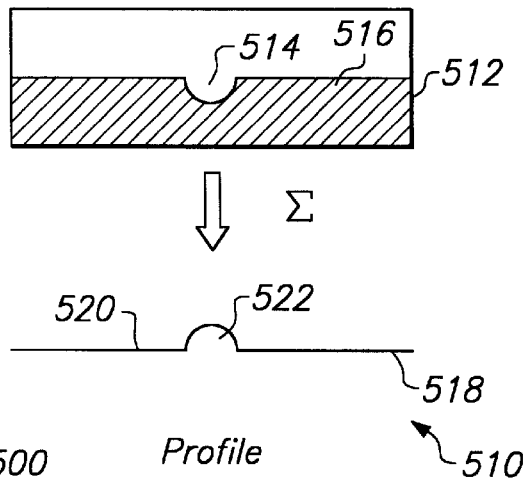
Figure 11C:
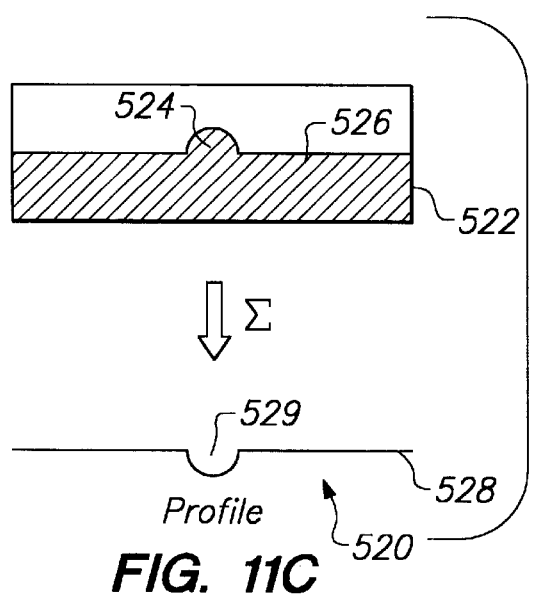
Figure 12A:
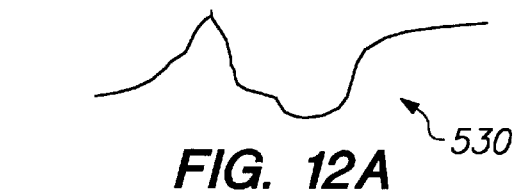
FIGS. 12A through 12D illustrate possible resulting intensity profiles for the flux source image of FIG. 11A depending upon the orientation of the system regions of interest used.
Figure 12B:
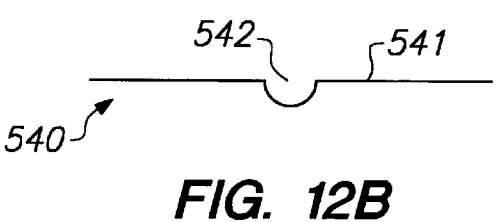
Figure 12C:
Figure 12D:

Examples of developed profiles for other types of defects are shown in FIGS. 11B and 11C. FIG. 11B shows a process 510 in which a region of interest 512 has an intrusion defect 514 into a line 516. Summing columns of pixels for this region of interest produces a profile 518. This profile also has a flat baseline 520 because the pixels are summed in columns perpendicular to the edge of line 516. The increase in intensity for profile 518 at 522 is caused by intrusion defect 514 which allows more flux to pass through, thus creating a greater intensity of light at defect 514 which creates a higher intensity 522 in profile 518.

FIG. 11C shows a process 520 in which a region of interest 522 has an extension defect 524 on a line 526. Summing columns of pixels for this region results in a profile 528 having a lower intensity in region 529 due to defect 524. It should be appreciated that developing a profile for other defects such as a hole defect, and for other features such as line widths may be performed in a similar manner.

FIGS. 12A–12D illustrate examples of profiles that may be developed for a spot defect using the regions of interest shown in FIGS. 10A–10D, respectively. FIGS. 12A–12D show profiles 530, 540, 550 and 560, that have widely varying intensity distribution profiles for their corresponding regions of interest. Only profile 540 of FIG. 12B has a high quality profile in which the baseline 541 is flat and the feature region 542 of the profile will be proportional to the area of the feature. These varying profile results illustrate how multiple regions of interest can be used to find a high quality profile. Certain regions of interest may produce a poor profile, while others may produce a good profile. Thus, the use of multiple regions is advantageous. The development of statistics for each profile in order to find the best profile will be explained below with reference to FIGS. 8C and 8D.

Once an intensity distribution profile has been formed for a region of interest, in step 426 this profile is added to a profile list for later reference. Control then returns to step 420 and other profiles are developed for the remaining regions of interest. Once profiles have been developed for each of these regions of interest, the quality of the profiles can be evaluated by developing profile statistics.

Figure 8C:
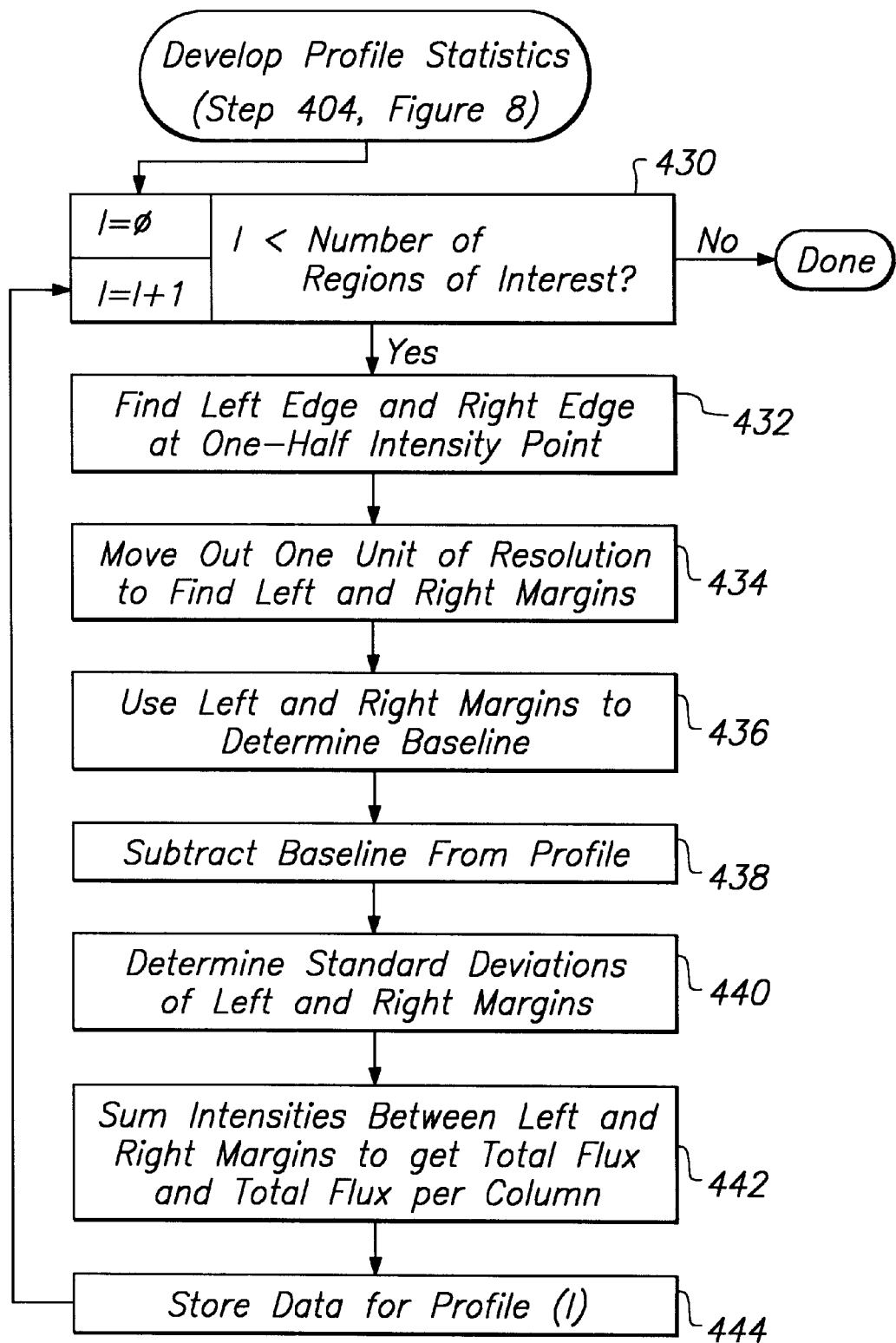
FIG. 8C is a flowchart for the develop profile statistics step of FIG. 8.

Development of profile statistics will now be explained with reference to FIG. 8C and FIG. 13. FIG. 8C is a flowchart illustrating a technique for the development of profile statistics. FIG. 13 shows in greater detail an intensity distribution profile 600, similar to either of the profiles of FIG. 11A or FIG. 12B. Profile 600 has been formed from a particular region of interest surrounding a spot defect or extension defect. It should be appreciated that profile 600 is an example of a profile and that various feature types may result in profiles of different forms. Profile 600 is plotted on a graph having an intensity axis 602 and a distance axis 604. Profile 600 has a feature region 606 containing the summed intensities of the pixels for particular columns within the feature to be measured. Profile 600 also has a baseline 608 and left and right margin portions 610 and 612.

Returning now to FIG. 8C, a technique for developing profile statistics will now be described. Step 430 loops through each of the profiles developed for each region of interest. Once statistics have been developed for all profiles then step 404 is done.

In developing profile statistics the use of a unit of resolution for the optics being used is helpful. In one embodiment of the invention, a Blur Size is determined empirically to estimate the resolution unit. In one embodiment, the Blur Size may be empirically determined as follows. Using a good quality profile having a fairly horizontal baseline, measurements are taken at 20% of the maximum intensity 630 and at 80% of the maximum intensity 634. The number of pixels located horizontally within the range bounded by the 20% and the 80% values is determined to be the Blur Size 636 which is an estimate of the resolution unit. This is a valid approximation of a resolution unit because were the optics to be perfect and everything to be in sharp focus, the intensity would not drop off gradually from maximum to zero but would transition immediately. Thus, since blurring causes a gradual drop off of intensity, a measurement of a Blur Size from 20% to 80% of intensity is a reasonable estimation of the resolution unit. Of course, other values and techniques may also be used in order to determine a resolution unit.

In step 432 the left edge 620 and the right edge 622 of profile 600 are determined by finding these corresponding points at the one-half maximum intensity level 624. Next, in step 434 a distance equal to one resolution unit 640 and 642 is measured from the left edge 620 and from the right edge 622 respectively, in order to determine an edge of the left margin 644 and an edge of the right margin 646. The corresponding outer edges 648 and 650 of the left and right margins respectively, are determined by finding points 652 and 654 at 5% of the maximum intensity 626, respectively, of profile 600.

Once the left margin portion 610 and the right margin portion 612 have been defined by locating their respective edges, the average of the intensity values along these two margins is used to form a baseline intensity 608 in step 436. Next, in step 438 baseline intensity 608 is subtracted from profile 600 in order to leave only feature region 606. Subtracting the baseline has a similar effect as step 270 of FIG. 7, in that background material is subtracted out. That is, the intensity values not due to the presence of a feature are removed. The advantage of subtracting a baseline is that no reference image need be obtained. More specifically, subtraction of a baseline accommodates for uneven illumination or slight rotation between the lines on the mask and the region of interest. These cause the baseline to be tilted but straight. After baseline subtraction, the margins yield a low standard deviation as described in the following paragraph.

In step 440, the standard deviations for the left and right margin intensities are determined in order to give an indication as to how flat the baseline is, which in turn indicates whether the profile is of good quality and would return an accurate flux reading. For example, a low standard deviation indicates a good baseline, while excess noise in the data would cause data points to have a larger deviation from the mean and result in a poorer baseline. In step 442 the intensities between edge 644 of the left margin and edge 646 of the right margin are summed in order to compute the total flux that passes through the feature. This total flux can then be used to determine the area of the feature or other dimensions.

The total flux is also computed to assist in determining the height of the feature or its line width. For line width, the total flux yields the area for the region of interest, which corresponds an area of a portion of the line to be measured. For example, FIG. 10E shows an area 395 of line 392. If the total flux is determined, this yields the value for area 395. Dividing this area value by the ROI height 391 yields the line width 394.

Height of a feature can also be determined from the total flux of one column of the profile. Dividing the total flux by the intensity range yields the area of that column. If an assumption is made that the defect is opaque (or totally clear), then the area of that column leads to a height measurement because the column is one pixel wide. Thus, the height is equivalent to the area.

Once the flux and the standard deviation have been computed for the profile, this data for the profile is stored for later reference in step 444. Control then returns to step 430 in which statistics are developed for any remaining profiles.

Figure 8D:
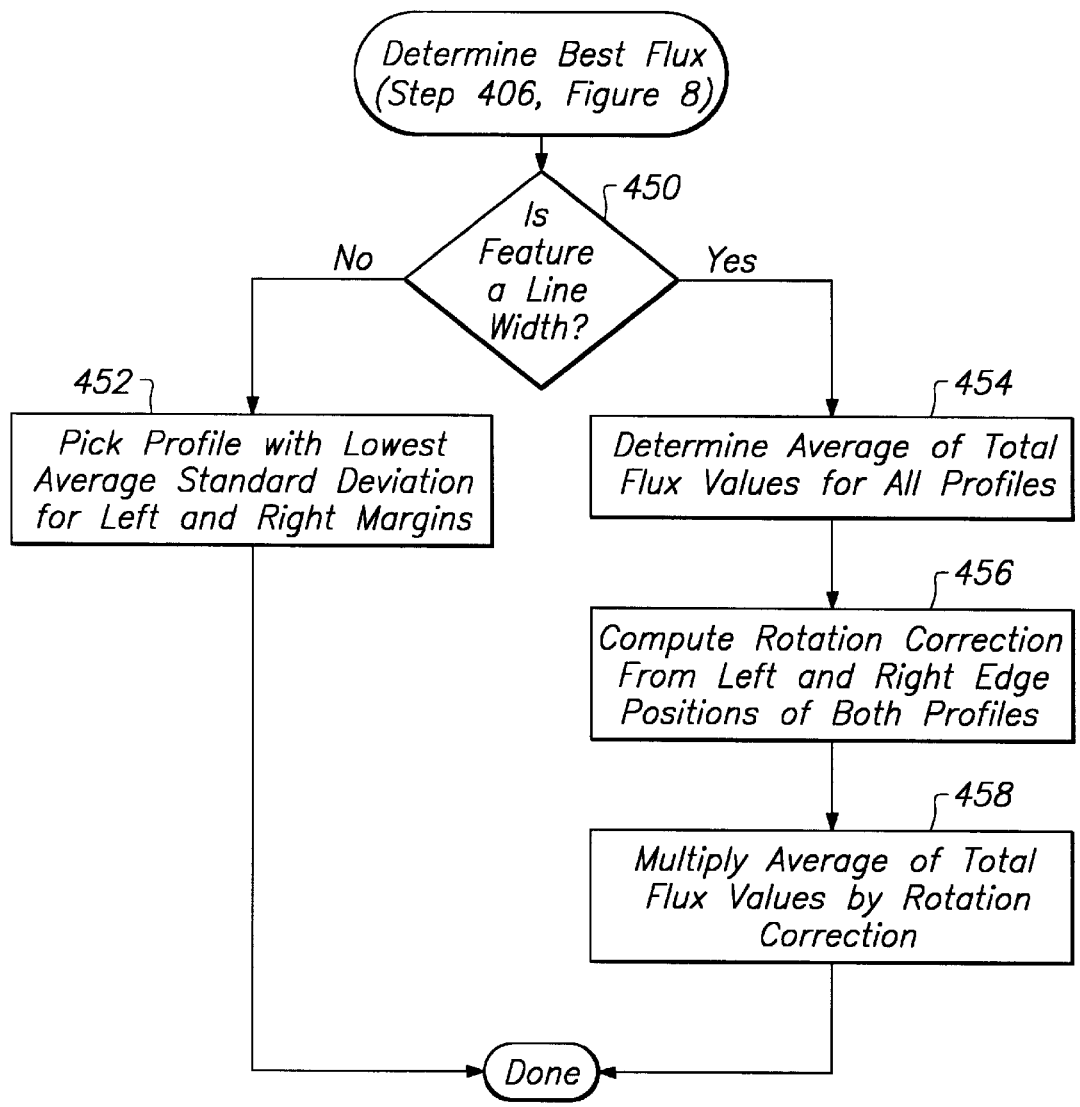
FIG. 8D is a flowchart for the determine best flux step of FIG. 8.

FIG. 8D illustrates an embodiment of the determine best flux step of FIG. 8. The best flux measurement will be determined by reference to the profile statistics developed for each profile in FIG. 8C. Step 450 determines whether the feature is a defect or line width. If the feature is a defect, then the profile with the lowest average standard deviation for the left and right margins is picked and the total flux measurement associated with that profile is returned to FIG. 6 as the determined flux for the defect. Only one of the profiles is picked in step 452 because only the profile with the lowest standard deviation for the margins will have the best and most accurate flux measurement for the defect. That is, only the best profile will have a total flux measurement that is proportional to the area of the defect.

As can be seen with reference to FIGS. 12A through 12D, various orientations for regions of interest produce wildly varying profiles. Since profile 540 of FIG. 12B (for example) has a relatively flat baseline 541, the average standard deviation for its left and right margins will be extremely low, indicating that this profile provides a feature region 542 having a flux measurement that most accurately reflects the flux passing through or being blocked by the defect. Once this profile and flux are determined in step 452, step 406 is done.

On the other hand, if the feature is a line width, then in step 454 the average of the total flux values for all profiles is determined. In step 454 the average of the total flux values is determined instead of picking a profile with the lowest standard deviation because the two regions of interest produced for a line width (as shown in FIG. 10E) are both at the same angle to the line and will produce nearly similar profiles and total flux values. In step 456 a rotation correction is computed from the left and right edge positions of both profiles in order to compensate for a line that may be angled. This rotation correction may be performed in a wide variety of manners. By way of example, the following formulas may be used:

theta=fabs(atan*2(Measured Center Difference, ROI Spacing Distance))

theta correction=cosine(theta)

where Measured Center Difference is the difference between the left hand edge positions of the profiles for each region of interest and ROI Spacing Distance is the distance in pixels between the two regions of interest.

Next, in step 458 the computed rotation correction (theta correction) is multiplied by the average of the total flux values in order to determine the correct flux measurement for the measured line width. Step 406 is then done.

Figure 14:
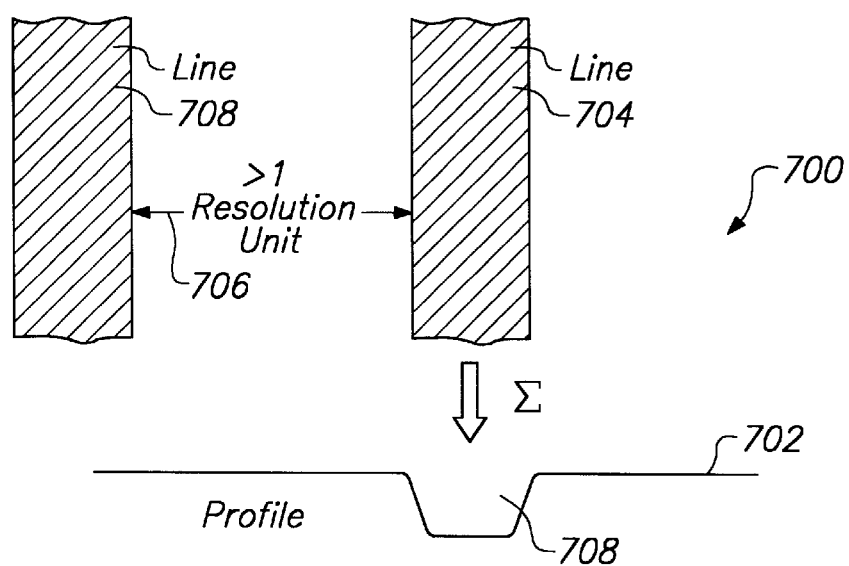
FIG. 14 illustrates the development of an intensity profile for a width of a line that is separated by greater than one resolution unit from another line.

In certain circumstances another technique may be used to develop a profile for determining a line width. This technique will now be discussed with reference to FIGS. 14 and 15. FIG. 14 shows a process 700 of developing a profile 702 for a line 704 that is greater than a distance 706 of one resolution unit from another line 708. As long as the two lines 704 and 708 are separated by a distance greater than one resolution unit, then summation of the pixels within the line region 704 results in a good profile 702 having a feature region 708 which corresponds to the width of line 704.

Figure 15:
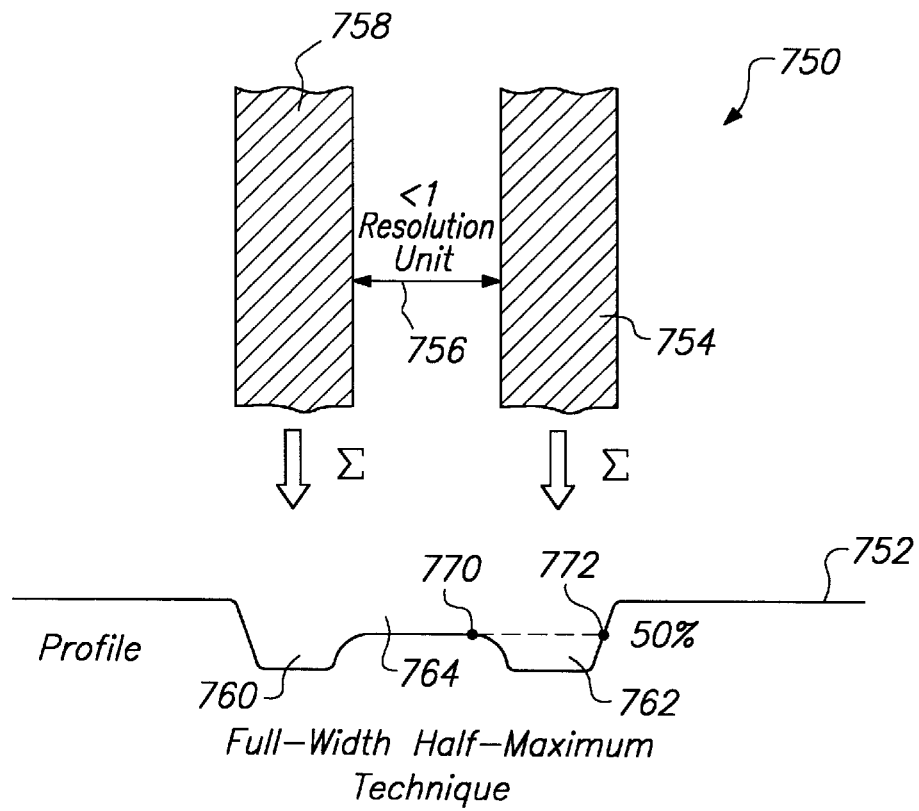
FIG. 15 illustrates a full-width half-maximum technique for developing an intensity profile for the width of a line that is at a distance of less than one resolution unit from another line.

By contrast, FIG. 15 illustrates a process 750 of developing a profile 752 for a line 754 which is at a distance 756 from line 758 that is less than one resolution unit. In this example, because the two lines are separated by less than one resolution unit, profile 752 results in having a feature region 760, a feature region 762 and an intermediate region 764 which together do not correspond to the width of line 754. This enlarged feature region formed by regions 760, 762 and 764 occurs because the two lines are closer than one resolution unit apart. Such a combined region is not useful for developing a good baseline without further processing.

However, by using a full-width half-maximum technique, a feature region 762 may still be defined that does correspond to the width of line 754. In this technique, points 770 and 772 at 50% of the intensity of the profile are defined that then correspond to the left and right edges of the appropriate feature region. Once this feature region has been defined, feature region 762 may then be analyzed as described above with reference to FIGS. 8C, 8D and 13 in order to develop profile statistics and produce a flux measurement that is indicative of the true width of line 754. If such a technique is used, then four additional calibration plots would be used in order to provide calibration data for each of the four types of line widths that are measured using the full-width half-maximum technique.

Development of separate calibration plots for use in measuring line widths that are closer than one resolution unit to other lines or features is advantageous because of non-linearities associated with these types of measurements. Non-linearities occur in part because the closeness of other features causes measurement of the line in question to be distorted. Development of a polynomial calibration curve for measuring these types of line widths results in a much more accurate determination of the line width.

GENERAL OPACITY, WIDTH AND HEIGHT MEASUREMENT DESCRIPTION

As described above in the Summary, the ability to accurately measure the opacity, width and height of a feature having dimensions on the order of a micron and less is advantageous. The following description presents embodiments for measuring those dimensions.

FIG. 19 is a graph 780 illustrating contrast versus diameter for an opaque material. Graph 780 shows an opacity curve 782 representing the perceived contrast for an opaque material in relation to its diameter. Opacity curve 782 illustrates that an opaque material (such as a chrome spot defect) having a diameter substantially greater than the wavelength of light will fall on opacity curve at point 784 or farther out (100% contrast). I.e., at point 784 (and for opaque materials greater than this diameter) an opaque material has a contrast of 100% with its background. Of course, for a feature having a diameter of zero, the contrast will be 0% with its background. In between these two points, however, the contrast for an opaque material against its background will vary between 0% and 100%.

One reason is because the size of such a feature is close to that of the resolution of the optics being used. In other words, the blurring of a feature whose size is close to, or less than, the resolution results in a contrast for that feature that is less than 100% even though the feature may be perfectly opaque. For example, point 786 represents a spot or hole defect that has a diameter close to 0.5 microns and has a contrast with its background of about 60% or so.

Advantageously, the present invention recognizes that materials that are less than perfectly opaque will fall at a point off of the opacity curve when their contrast is compared to their measured diameter. For example, a spot defect that is partially transparent (such as dirt or other substance that is not perfectly opaque) will end up producing more light flux that is received by a camera. Because more light flux is received (as opposed to a perfectly opaque spot defect), the spot defect will appear smaller in diameter than it truly is. In addition, because the spot defect is not perfectly opaque, its contrast will be lower than the contrast of a perfectly opaque spot defect. Point 788 represents the measured diameter of a semi-transparent spot defect that has a measured diameter of approximately 0.2 microns. Its contrast is approximately 30 percent. However, this measured diameter and contrast are somewhat lower than they should be due to the blurring effect and the semi-transparency of the spot defect. By taking into account these measured values and opacity curve data for a truly opaque spot defect, the present invention is able to determine the percentage opacity of the spot defect and thus correct measured dimensions of the defect.

Figure 27:
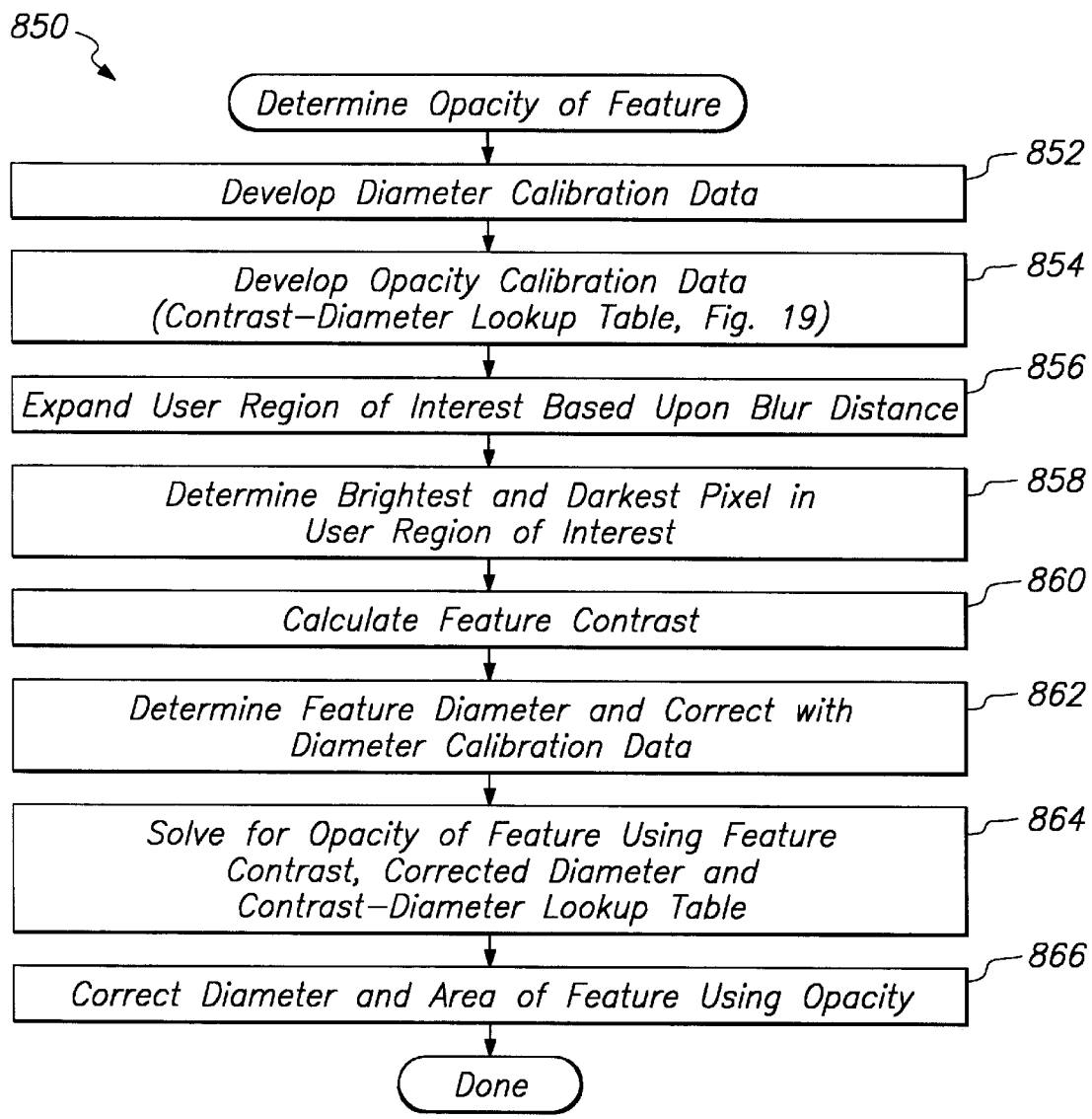
FIG. 27 is a flowchart illustrating one embodiment by which the opacity of a feature is determined.

A variety of techniques may be used to solve for the opacity of the spot defect using the above information. By way of example, FIG. 27 illustrates one embodiment that solves empirically for the opacity. In this embodiment of the invention, a measured spot defect that produces point 788 has its opacity adjusted until it falls at point 790 on the opacity curve. An adjusted opacity that produces point 790 is determined as the correct opacity of the spot defect. Solving for the opacity given the above information can also be done analytically or using other similar techniques.

Figures 20, 21:
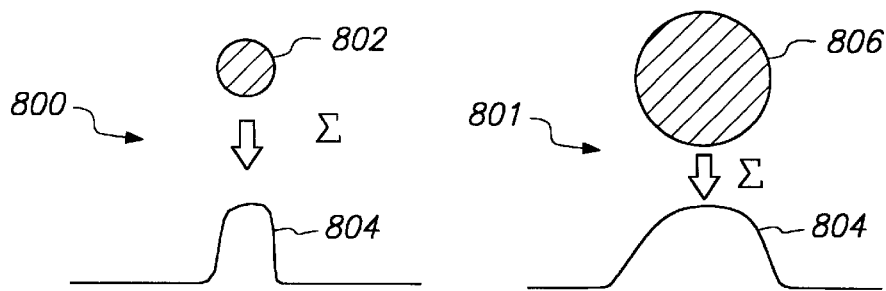
FIG. 20 illustrates the development of an intensity profile for a spot defect.
FIG. 21 illustrates the development of an intensity profile for a relatively larger spot defect.

FIGS. 20–23 illustrate a technique for determining the width of a feature. FIG. 20 illustrates the development 800 of an intensity profile for a feature. In particular, intensity profile 804 is developed from spot defect 802. Profile 804 is relatively sharp, i.e., has a high curvature value. FIG. 21 illustrates the development 801 of an intensity profile 808 for a relatively larger spot defect 806. Profile 808 is relatively flat, i.e., has a low curvature value. As can be seen from the two figures, a smaller defect produces an intensity profile having a sharper curvature compared to that of a larger defect. This observation allows the width of a feature to be calculated from its profile's curvature as will be described below in FIGS. 22, 23, and 28.

Figure 22:
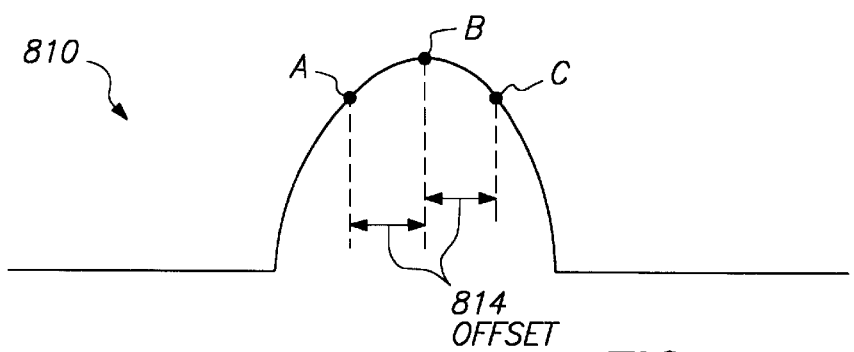
FIG. 22 is an intensity profile for a feature that illustrates a curvature calculation according to one embodiment of the invention.

FIG. 22 is an intensity profile 810 for a feature that illustrates a curvature calculation. Points A, B and C represent intensity values and are located on intensity profile 810. Point B is located at the profile peak while points A and C are located at an offset from the peak in a horizontal direction. The curvature of the profile may then be calculated using the formula: curvature=B*2-(A+C). Once the curvature for the intensity profile has been calculated, this number is used to determine the width of the feature as explained below.

Figure 23:
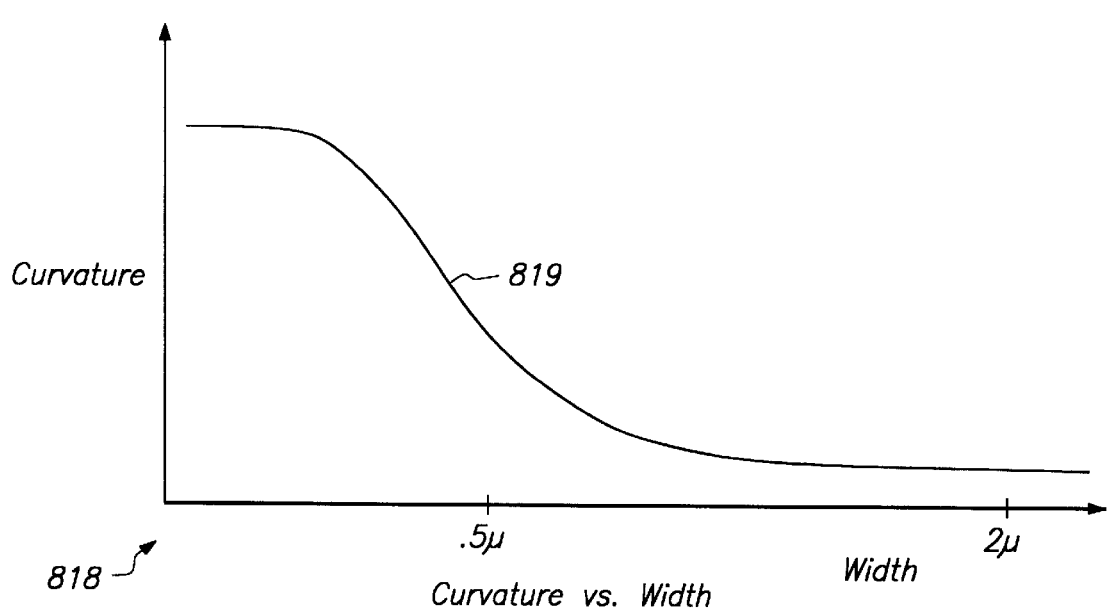
FIG. 23 illustrates a curvature versus width graph used to determine the width of a feature.

FIG. 23 illustrates a curvature versus width graph 818 illustrating how a calculated curvature of a profile is used to determine the width of the feature. Graph 818 has a curve 819 representing the relationship between the curvature of a profile of a feature and the width of the feature. As can be seen from curve 819, larger features having a width of about 3 or 4 times the wavelength of light will have a curvature value closer to zero, while curvature increases for extremely small features that have a width close to or less than the wavelength of light. By taking the calculated curvature from intensity profile 810 and fitting it to curve 819, a width may be determined for the feature. In a preferred embodiment of the invention, curve 819 is represented in a lookup table; it may also be represented in an equation.

Figure 24:
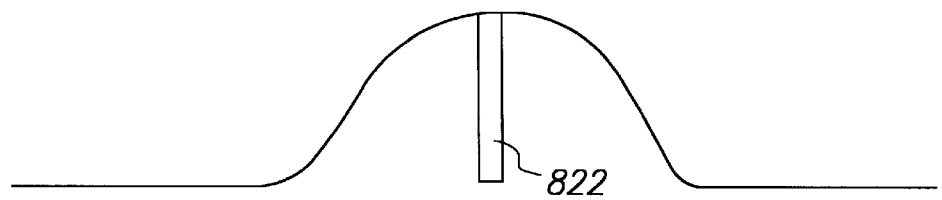
FIG. 24 is an intensity profile that has been calculated for any one of a wide variety of features that demonstrates how height may be measured.
Figure 25:
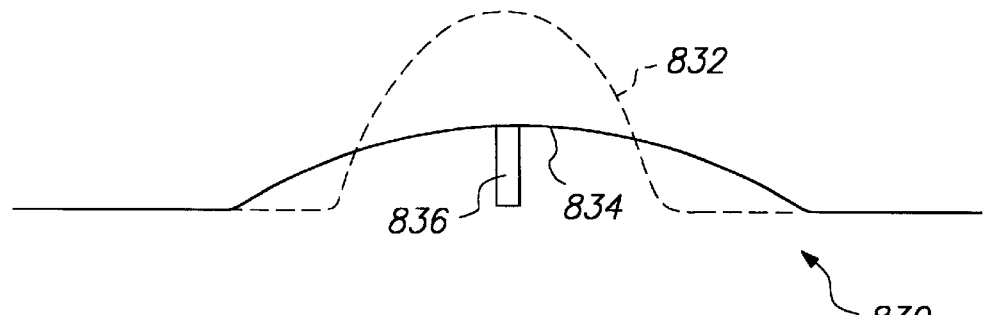
FIG. 25 illustrates a profile for a feature having a size close to the wavelength being used and a height measurement.
Figure 26:
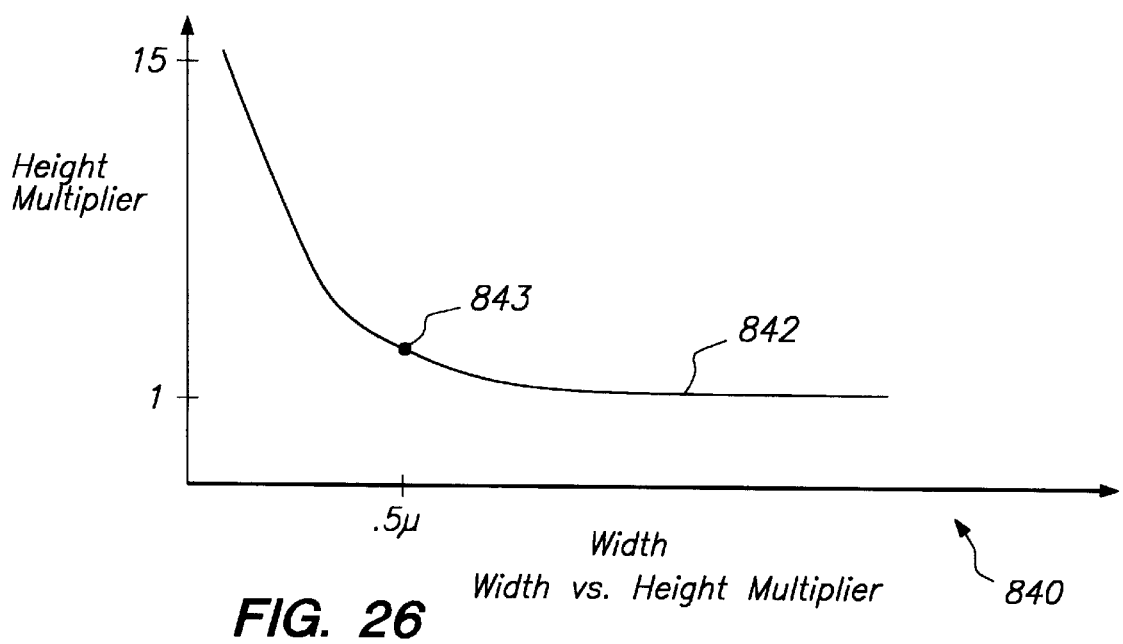
FIG. 26 is a width versus height multiplier graph used for determining the height of a feature.

FIGS. 24–26 illustrate a technique for determining the height of a feature. FIG. 24 is an intensity profile 820 that has been calculated for any one of a wide variety of features. Profile 820 represents the profile of a feature of a size of about greater than 1 micron and is useful in calculating the height of the defect. Column 822 is a one pixel wide column of light intensity centered at the peak of profile 820. As described earlier in the specification, summation of multiple columns of light intensities allows an area for the defect to be calculated. Because column 822 is one pixel wide, the area of region 822 is proportional to the height of the defect. In this fashion, the height of defects having sizes of about 1 micron or greater can be calculated using the techniques described earlier in the specification.

However, for features that are approximately less than 1 micron in size (i.e., whose sizes are closer to the wavelength of light), the blurring effect makes a straightforward measurement of the height of these features more difficult. Blurring also occurs for measurement systems using a particle beam where the features are closer to resolution of the microscope.

FIG. 25 illustrates profiles 830 for a feature having a size close to the wavelength of light being used. Profile 832 represents a true profile if one could be obtained and is proportional to the true height of the defect. However, due to the blurring effect, profile 832 ends up with a shape as shown by profile 834; it is somewhat more flattened out than what would be expected. The flux measured, or area under the profile, will be the same for each profile. However, relying upon the area of column 836 in order to determine a height for a feature that is less than about 1 micron in size returns a value for height that is somewhat less than the true height of the defect. In order to obtain the true height of such a feature, an embodiment of the invention uses a height multiplier.

FIG. 26 is a width versus height multiplier graph 840 that shows a curve 842 representing the relationship between the measured width of a feature and an appropriate height multiplier to use. Once a width has been determined for a feature as described in more detail in FIG. 28, the height multiplier obtained from curve 842 is multiplied with the measured height in order to obtain the true height of a feature. As can be seen from curve 842, features having a width of about greater than 1 micron have a height multiplier of one. As represented by point 843, a feature having a width of about 0.5 micron has a height multiplier of about 2, and features that are somewhat smaller than 0.5 micron have a height multiplier that approaches a value of about 15. The data represented by curve 842 is preferably stored in a lookup table. Derivation of the data is explained in more detail with reference to FIG. 29.

OPACITY, WIDTH AND HEIGHT DETAILED CALCULATIONS

The determination of opacity, width and height for any of a variety of features and/or defects will now be explained in more detail with reference to the following figures. Although determination of these quantities are presented in a particular order, this order is for illustrative purposes only and these values may be calculated in other orders as well. Furthermore, it should be appreciated that these calculations are applicable to a wide range of sizes of features and defects. As explained above, the present invention is especially applicable for determining opacity, width and height for features having sizes that approach, or are less than, the wavelength of visible light (about 0.5 microns). In general, the invention has been found to work well for features having sizes less than about 1 micron. More broadly, for other wavelengths of light and/or particle beams, the invention works well for features having sizes that are about or less than the wavelength being used.

As explained above, the determination of opacity for a feature assists in correcting for a measured area, width, height and/or other dimension of a feature that is not perfectly opaque. Although a determination of opacity is optional, calculation of an opacity value is helpful in correcting measured dimensions of features that are less than perfectly opaque. Furthermore, an opacity calculation may be used on isolated defects such as spots or holes, as well as on edge defects. Calculation of the opacity for an isolated defect is more straight forward because of the stark contrast between an isolated defect and its background. Calculation of opacity for an edge defect has been found to be best performed after reference subtraction. For example, a reference image for a chrome line is subtracted from the actual image of the line with the defect in order to produce the defect by itself against a stark background. This technique of alignment and reference subtraction for edge defects better allows the contrast and thus the opacity to be measured. Furthermore, measurement of opacity helps in determining what a feature is made of in addition to assisting in correction of a dimension measurement. For example, "hard" features of an opacity of about 100% can be assumed to be of metal or similar material, while "soft" features of a lesser opacity are more likely of a less opaque substance such as dirt.

FIG. 27 is a flowchart 850 illustrating one embodiment by which the opacity of a feature is determined and thus a dimension of the feature can be corrected. In step 852 calibration data for adjusting a measured diameter (or other dimension) of the feature is developed for use in compensating for lens optics, machine characteristics, blurring, etc. In a preferred embodiment of the invention, this step is performed as described in step 202 of FIG. 4 above and allows a measured value in pixels to be converted to a correct value in microns.

Step 854 develops calibration data for use in determining the opacity of the feature. This opacity calibration data may appear in an opacity curve as shown in FIG. 19. In a preferred embodiment of the invention, this opacity calibration data is stored in a contrast-diameter lookup table. To develop this opacity calibration data, a number of truly opaque features of different diameters each have their contrasts measured to produce the opacity curve of FIG. 19 and/or the contrast-diameter lookup table. The contrast-diameter lookup table thus provides the percentage contrast for a feature of any size that is truly opaque. As will be described below, this table is useful for determining the opacity of features that are less than perfectly opaque. In one embodiment of the invention, step 854 develops a different lookup table for each type of defect or feature. Preferably, one lookup table is developed for spots and one for holes. Two tables are developed because some cameras are not linear and have more gain in dark or bright areas. If the camera is linear, typically the two tables are the same.

Next, a user region of interest is developed around the feature to be measured. In a preferred embodiment of the invention, the user region of interest is developed as described in steps 204–208 of FIG. 4. In step 856 this user region of interest is expanded in both directions based upon the blur distance of the lens. Expanding the user region of interest allows for the smearing effect caused by very small features having a size close to the wavelength of light. In a preferred embodiment of the invention, the region is expanded in each direction by one blur distance. Each lens may have a particular value of a blur distance associated with it. In step 858 the intensity values for the brightest and darkest pixel in this expanded user region of interest are determined.

Step 860 calculates the feature contrast within this region preferably by subtracting the dark pixel value from the bright pixel value and dividing the result by the image intensity range. Preferably, the image intensity range for the region is determined as shown in the example of FIG. 7A above. For those features that are less than perfectly opaque, the calculated feature contrast value will be less than what might be expected.

Step 862 determines the diameter of the feature (or other dimension). Determining the feature diameter may be performed in a variety of ways similar to those described in the present application. Preferably, the feature diameter is determined as described above in step 210 of FIG. 4. Next, the feature diameter is corrected with the previously developed diameter calibration data such as is described in step 212 if FIG. 4. It should be appreciated that step 862 could also be performed earlier in the overall process. For features that are perfectly opaque, it is expected that the determined diameter and the calculated feature contrast will produce a data point that lies on or very near to the opacity curve of FIG. 19. For those features that are less than perfectly opaque, it is expected that such a data point will lie off of the opacity curve, for example point 788.

Step 864 solves for the opacity of the feature using the previously calculated feature contrast, the diameter determined from step 862 and the previously developed contrast-diameter lookup table from step 854. It should be appreciated that at this point opacity may be solved for using a variety of techniques using the information at hand. By way of example, opacity may be determined analytically by developing a formula. Preferably, solving for opacity is done empirically using Newton's method.

Using Newton's method, opacity may be determined as follows. Because the opacity of the feature is less than 100%, its contrast will be less than expected. Also, its measured diameter will be less than expected because the semi-transparency of the feature allows more flux to reach the optics, resulting in a smaller calculated area and diameter. Thus, a data point based upon the two would not necessarily fall upon the opacity curve of FIG. 19. Given the data point off the curve, one may empirically take guesses at the percentage opacity of the feature to see which would have resulted in the data point falling on the curve. Once a correction for an opacity value has been found that places the data point on the opacity curve, the correct opacity has been determined. As mentioned above, this iterative process is preferably performed using Newton's method and the contrast-diameter lookup table developed in step 854.

Once the opacity of the feature has been determined, then step 866 corrects the measured diameter or area of the feature. Preferably, the correct area is determined by dividing the measured area by the opacity, and the correct diameter is determined by dividing the measured diameter by the square root of the opacity. For a measured height that is determined as described below, its value may be corrected by dividing the measured height by the opacity.

Figure 28:
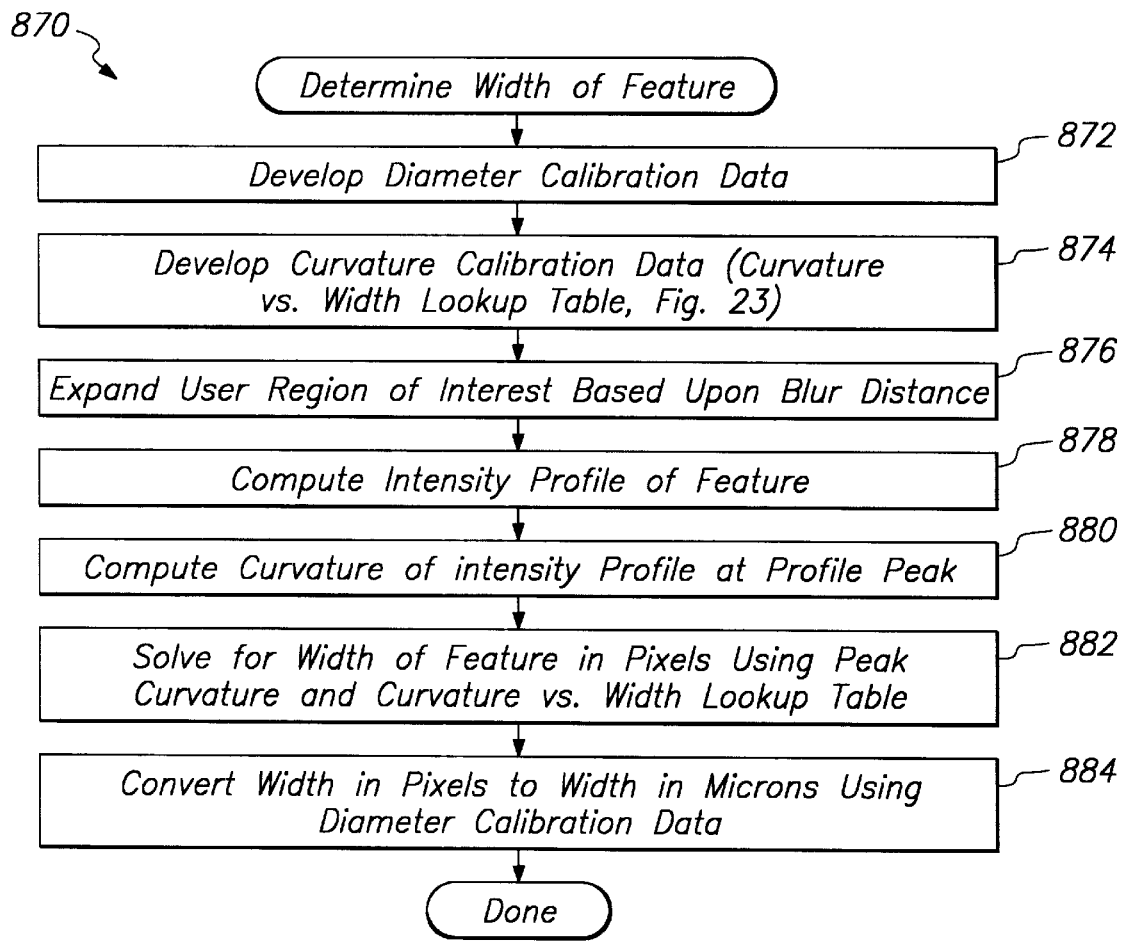
FIG. 28 is a flowchart illustrating a technique for determining the width of a feature according to one embodiment of the present invention.

FIG. 28 is a flowchart 870 illustrating a technique for determining the width of a feature according to one embodiment of the present invention. In step 872 calibration data for adjusting a measured diameter (or other dimension) of the feature is developed for use in compensating for lens optics, machine characteristics, blurring, etc. In a preferred embodiment of the invention, this step is performed as described in step 202 of FIG. 4 above and allows a measured value in pixels to be converted to a correct value in microns.

Step 874 develops curvature calibration data for use in determining the width of the feature. This curvature calibration data may appear in a curve as shown in FIG. 23. In a preferred embodiment of the invention, this curvature calibration data is stored in a curvature-width lookup table.

Prior art techniques have had difficulties in measuring the width of a feature at submicron sizes in a production environment. In one embodiment, the present invention overcomes this hurdle by developing data for the curvature-width lookup table by first measuring the area of defects which are known to be round. Even though these defects are of sub-micron sizes, an accurate area can be determined using the techniques described herein. It is then a simple matter to derive the width (or diameter) from the area for these known round defects. Once a width has been determined for a defect, the curvature of the intensity profile for that defect is calculated using the techniques described below in step 880. Now that a curvature and a width has been calculated for a number of these known round defects, these data points are stored in the curvature-width lookup table for future reference in step 882. A lookup table may be developed for each type of feature.

Alternatively, defects of known submicron widths (or diameters) can have the curvature of their profiles calculated for generation of data points for the curvature-width lookup table. Widths of submicron defects can be measured with an expensive, sophisticated machine such as an atomic force microscope.

Next, a user region of interest is developed around the feature to be measured. In a preferred embodiment of the invention, the user region of interest is developed as described in steps 204–208 of FIG. 4. In step 876 this user region of interest is expanded in both directions based upon the blur distance of the lens as described above in step 856.

Step 878 computes an intensity profile for the feature. An intensity profile may be computed in many ways. In a preferred embodiment of the invention, the profile is computed as described above from step 210 of FIG. 4 through step 402 of FIG. 8. If multiple intensity profiles are developed for a particular feature, then profile statistics may be developed as described in FIG. 8C in order to help choose the best profile. Step 880 computes the curvature of the intensity profile at the profile peak. By way of example, curvature is calculated as described in FIG. 22.

Step 882 solves for the width of the feature in pixels using the peak curvature calculated in step 880 and the curvature-width lookup table developed in step 874. By way of example, curve 819 of FIG. 23 is used to map a computed curvature value onto a width of the feature in pixels. As previously described, features with low curvatures will have a larger width, whereas features whose intensity profiles have a high curvature will have a relatively smaller width. Advantageously, the technique of the present invention allows for the calculation of width for features that are close to the wavelength of light in size. Step 884 converts this width in pixels to a width in microns using the diameter calibration data developed in step 872. As measurement of these small features improves, it is expected that a diameter calibration curve will become more linear and become optional.

Width may be determined in other ways. By way of example, for features of sizes of about 0.6 microns and greater the width can be determined using a full-width half-maximum technique. However, the curvature technique described above is preferred for sizes of features of about 0.5 microns and less.

Figure 29:
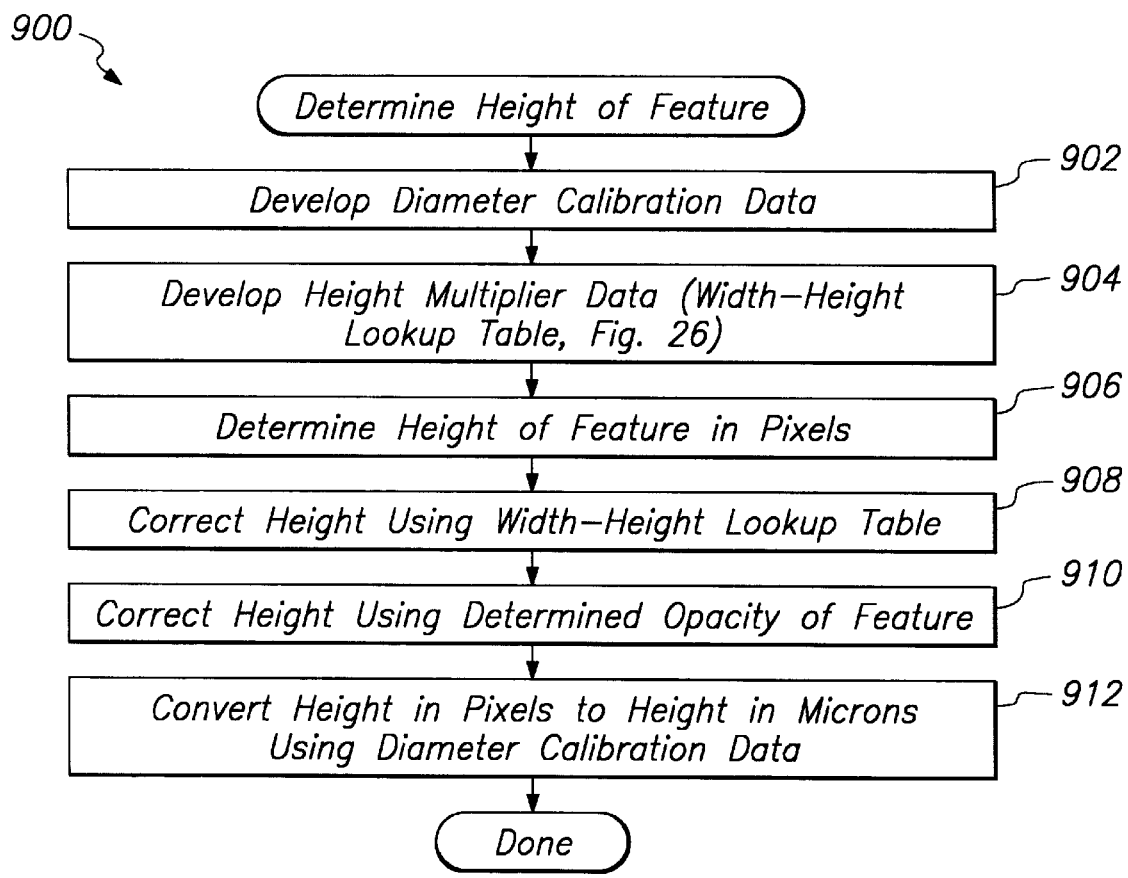
FIG. 29 is a flowchart illustrating one technique by which the height of a feature is determined.

FIG. 29 is a flowchart 900 illustrating one technique by which the height of a feature is determined according to one embodiment of the present invention. In step 902 calibration data for adjusting a measured diameter (or other dimension) of the feature is developed for use in compensating for lens optics, machine characteristics, blurring, etc. In a preferred embodiment of the invention, this step is performed as described in step 202 of FIG. 4 above and allows a measured value in pixels to be converted to a correct value in microns.

Step 904 develops height multiplier data useful for adjusting a measured height based upon the measured width of a feature. In one embodiment of the invention, the height multiplier is derived from measurements of a number of round defects of known sizes. For example, consider a known round defect having a diameter of 0.25 microns (from a VERIMASK, for example). Using techniques described herein, the area is measured and the diameter is determined. Alternatively, area and diameter need not be measured, but a the stated diameter of a feature (from another source) could be assumed to be the correct diameter. Preferably, the area and diameter are measured using the techniques described herein to return a more accurate result.

Of course, with a round defect, the diameter is also the height and width. Once the diameter is determined to be 0.25 microns, the height of the defect is measured using the techniques described in step 906. Optimally, this measured height should be the same as the measured diameter, but as described in FIGS. 24–25, the measured height will be smaller than expected. For example, the measured height might be 0.05 microns. By dividing the measured diameter of 0.25 microns by the measured height of 0.05 microns a height multiplier of 5 is obtained. Thus, it is now known that for defects having a measured diameter (or width) of 0.25 microns, that a height multiplier of 5 should be used to correct for a measured height. By measuring a number of known round defects of a variety of sizes a width vs. height multiplier curve such as is shown in FIG. 26 is developed. Preferably, data from such measurements are stored in a height multiplier lookup table. A lookup table may be developed for each type of feature.

In step 906 the height of the feature is measured in pixels. The height of a feature may be measured in many ways, in a preferred embodiment of the invention, height is measured as described in steps 204–210 of FIG. 4. Once height has been measured, this height is corrected for using the height multiplier lookup table in step 908. To use the table, the measured width (as calculated in FIG. 28, for example) is used to reference the appropriate height multiplier which is then multiplied with the height measured in step 906.

Because the feature may be less than perfectly opaque, in step 910 the height is also corrected for opacity by dividing the measured height by the opacity. Preferably, opacity is determined as described herein with reference to FIG. 27. Finally, in step 912 the corrected height value in pixels is converted to a value in microns using the diameter calibration data developed in step 902.

RADIUS OF CURVATURE GENERAL BACKGROUND

An embodiment of the present invention is also useful in determining the radius of curvature of a corner of a feature on a photographic mask. In general, this embodiment is useful for determining the radius of curvature of any corner of a wide variety of media, and is especially useful where the size of radius involved approaches, or is less than, about the resolution of the microscope.

In the process of manufacturing photomasks and other such products, the sharpness of feature corners is a useful indicator of the quality of the process. Generally sharper (lower radius) corners indicate better focus and process control. Thus measurement of corner rounding is commonly used for process control in manufacturing photomasks.

Presently corner rounding is measured by receiving an image of a corner at a known high magnification, and then overlaying templates with circles of different radii. The template circle that appears to match the corner best gives the radius of the corner after correction for the image's magnification.

Unfortunately, the small geometries now used in photomasks make these measurements difficult because light microscopes, which are preferred for their ease of use and speed, do not allow measurement of radii smaller than about 0.25 micron. Any corner, no matter how sharp, will appear to have a radius of 0.25 micron (or about one-half the resolution of the microscope). Instead, measurements are taken with higher resolution microscopes such as scanning electron microscopes (SEM), Focused Ion Beam (FIB) microscopes, Atomic Force Microscopes (AFM), or light microscopes using UV illumination. These methods tend to be expensive, slow, complicated, and are unsuitable for a production environment. Accordingly, it would be desirable to have a technique for accurate measurements of a corner radius with a size less than about the resolution of the microscope that is fast, inexpensive and suitable for a production environment.

RADIUS OF CURVATURE DESCRIPTION

Figure 30:
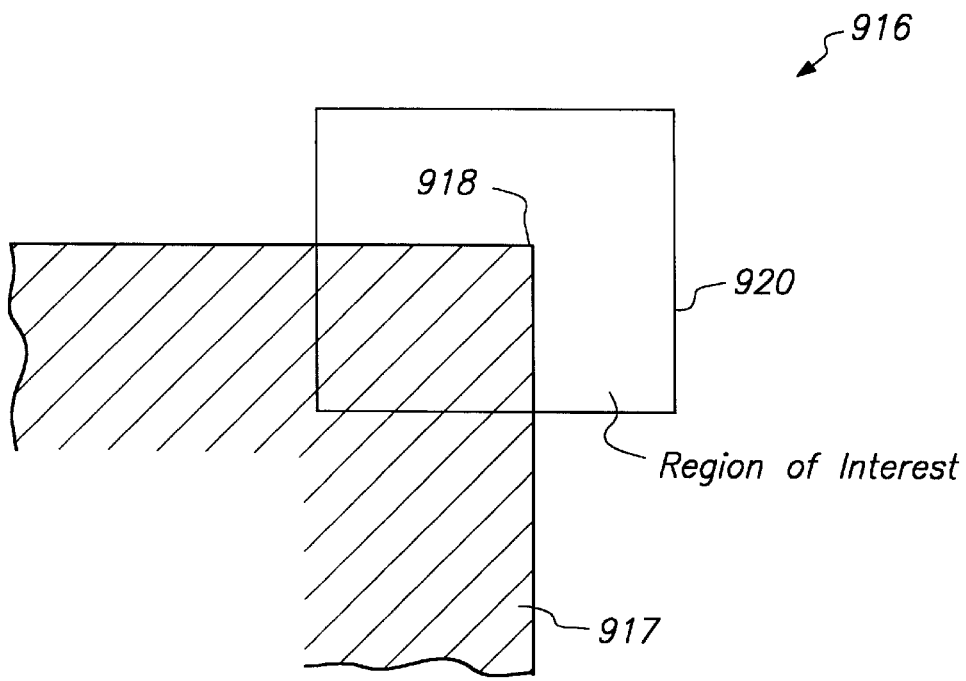
FIG. 30 illustrates a reference corner useful in determining the radius of curvature of an actual corner.
Figure 31:
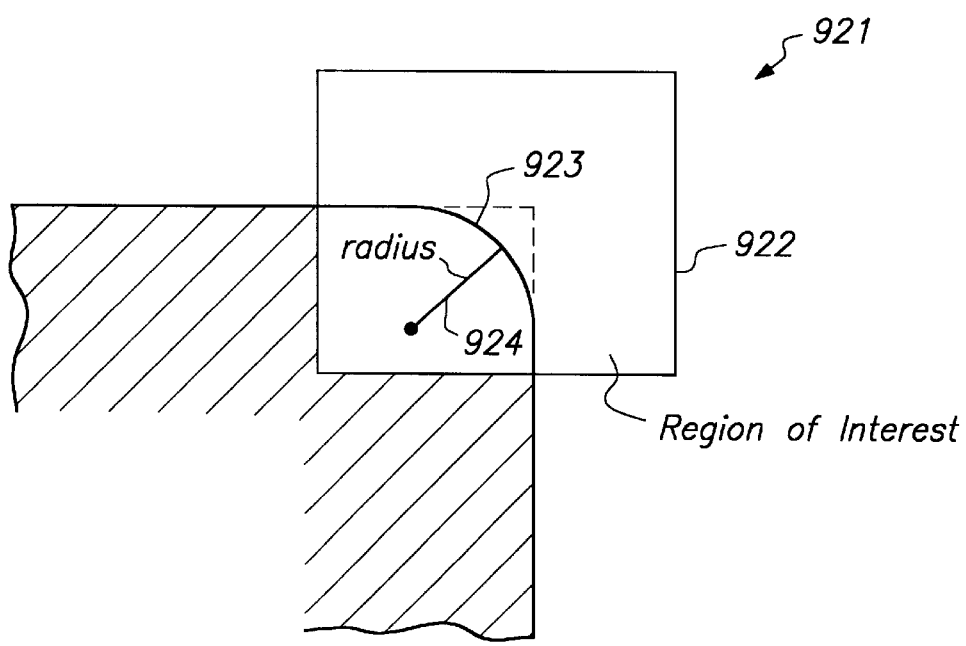
FIG. 31 illustrates an actual corner and its radius of curvature.

The method discussed herein can use conventional optical microscopes or imaging methods that provide a "bright field", or "dark field" image. As shown in FIGS. 30 and 31, the basic technique is to compute the flux area of a region 920 that includes a perfect (zero radius) corner 918, subtract the flux area of the corresponding region 922 containing the actual corner 923, and then compute the radius 924 from that difference.

In another embodiment, the flux area of a region that includes a reference corner of known radius is computed.

This flux area is then subtracted from the flux area of the corresponding region 922 containing the actual corner 923 to compute the radius 924 from that difference. Thus, steps 5–7 below of generating a reference corner would not need to be performed. Step 10 below would then be modified to determine the radius of curvature based on the flux area difference given that the reference corner has a known radius. For example, Radius=sqrt (4Alpi+(Radius of reference corner)^2).

Figure 35:
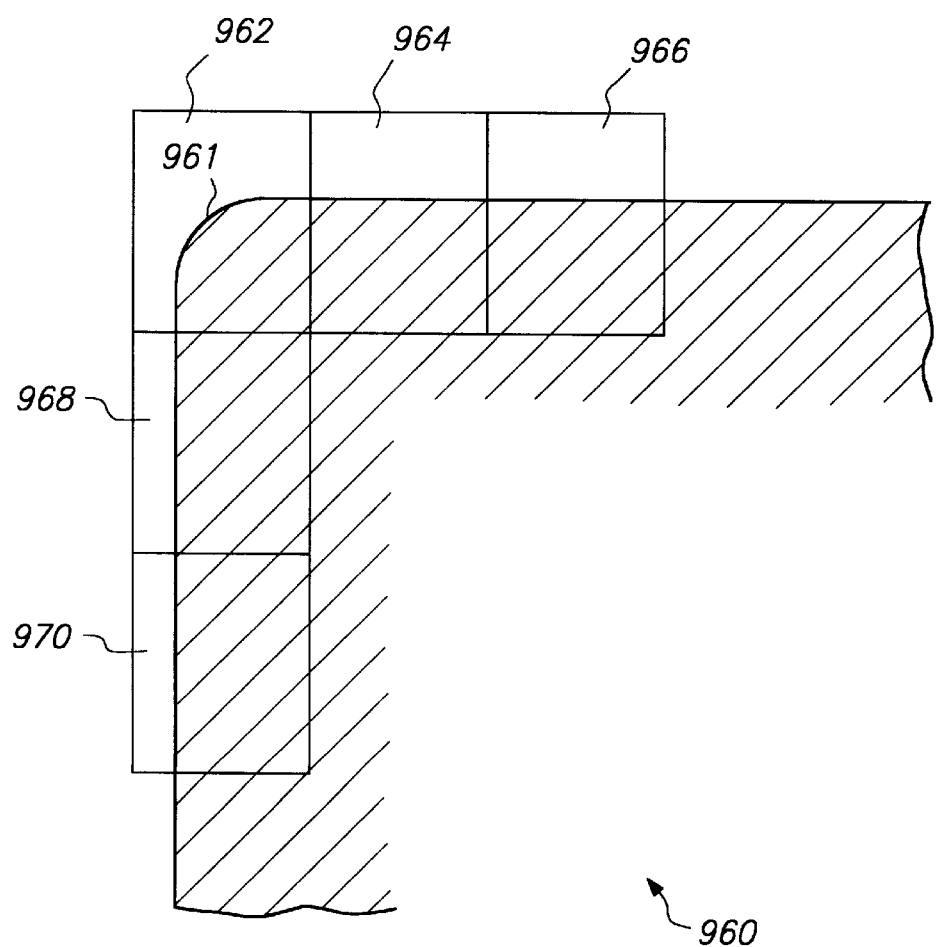
FIG. 35 illustrates an alternative embodiment for determining the radius of a corner.

An advantageous step is estimating the flux area of a perfect corner using the edges adjacent to it. For example, as shown in FIG. 35, this may be performed by replacing the corner region 962 with pixels or profile data extrapolated from data from the edge regions 964–970 suitably far from the corner (typically two blur distances). In a preferred implementation below this extrapolation is performed in steps 5 through 7.

The preferred implementation generates a reference profile for the corner region 962 of FIG. 35 by extrapolating and multiplying the profiles from regions 964–970 to produce a Corner Reference Profile, subtracting the measured profile for the corner region from the Corner Reference Profile, and computing the corner radius that would produce that flux difference.

Figure 32:
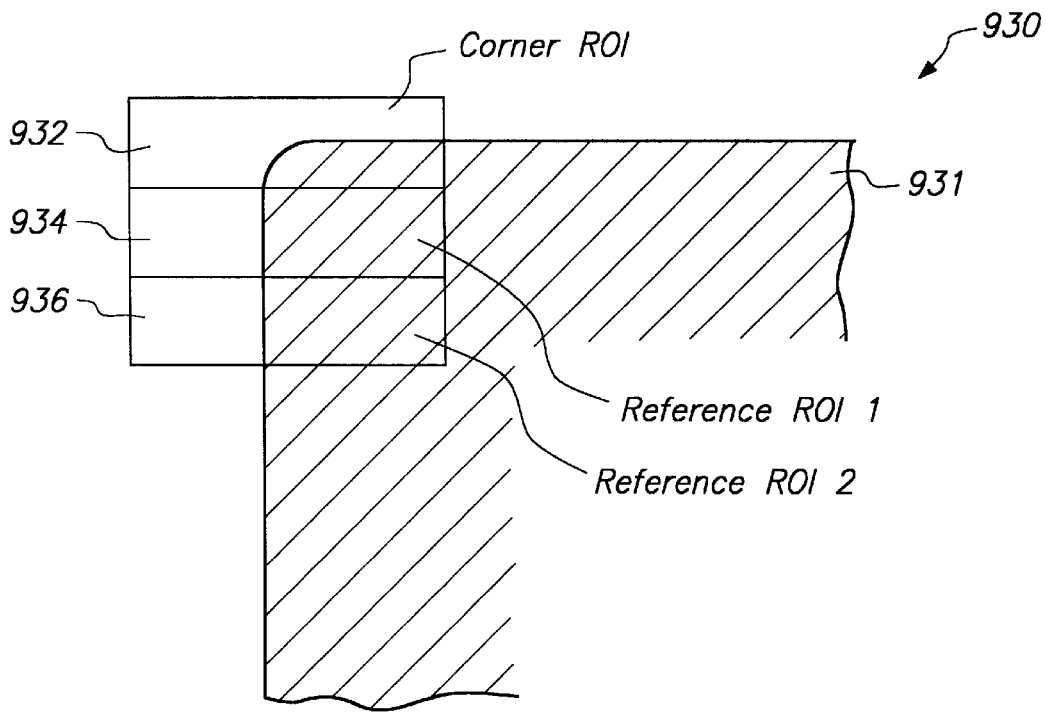
FIG. 32 illustrates regions of interest useful in determining the radius of a corner.

An embodiment uses the following steps to calculate the radius of curvature. A step 1 digitizes an image of the corner to be measured. Step 2 rotates the image so that the corner direction is as shown in FIG. 32. This can also be accomplished by suitable arrangement of the regions of interest (ROIs) described below. The rotation can be in increments of 90 degrees or fractional degrees. Step 3 defines three ROIs. One is the Corner ROI 932 with a width of 6 blur distances, a height of 4 blur distances, and a position of upper left corner being two blur distances above and left of the corner in the image. This position can be determined by the operator or with standard edge finding techniques. Two other ROIs are Reference ROIs 1 and 2, 934 and 936. Each has a size the same as Corner ROI and a position stacked below and adjacent to the Corner ROI.

Figure 33:
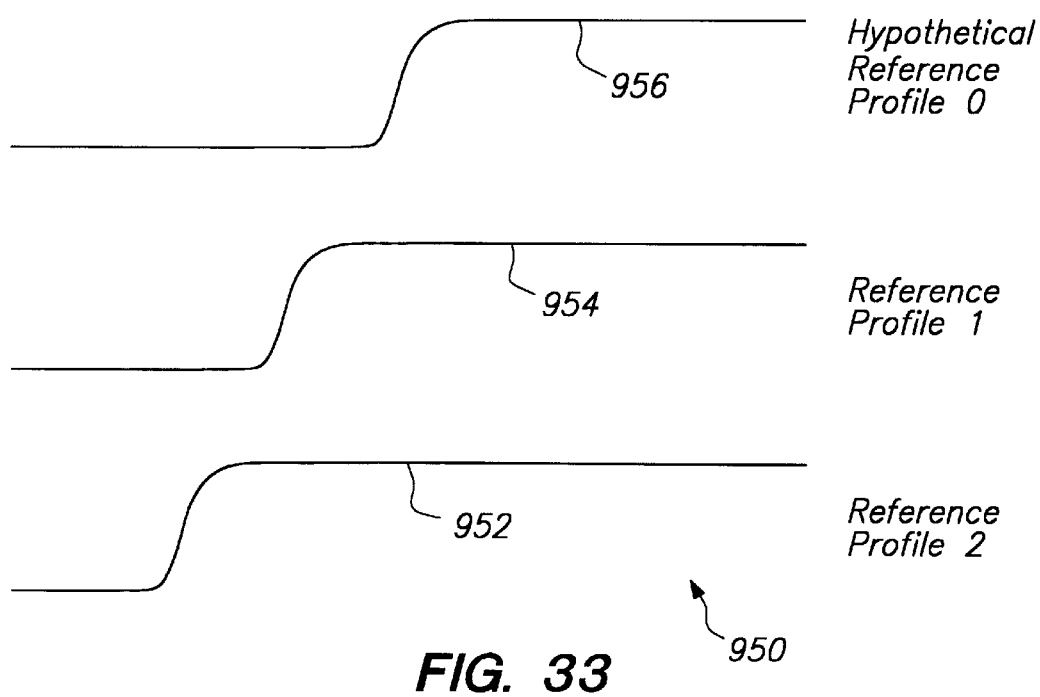
FIG. 33 illustrates profiles developed from the regions associated with a corner.
Figure 34:
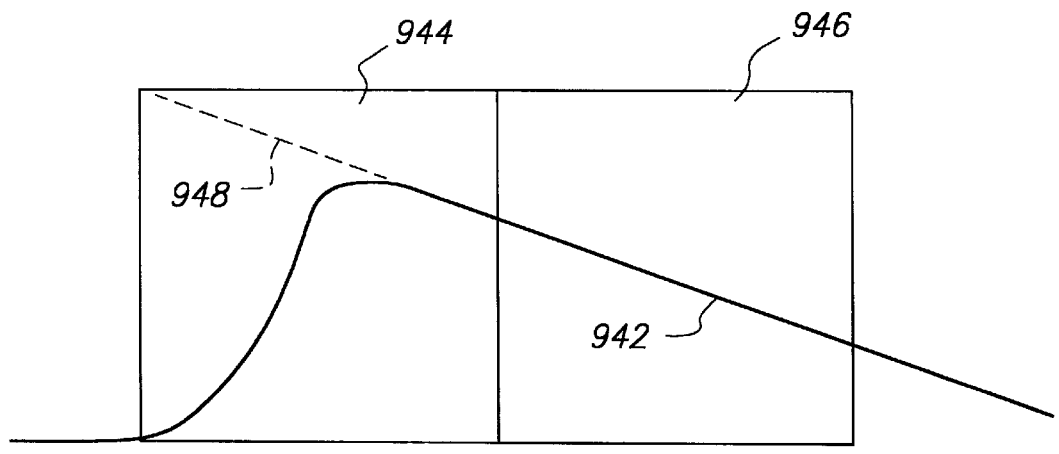
FIG. 34 illustrates another profile associated with a corner.

Step 4 takes intensity profiles of the three ROIs shown in FIG. 32. This produces the Corner Profile (FIG. 34, 942) and two Reference Profiles. As shown in FIG. 33, step 5 computes the hypothetical reference profile 0 956 which corrects the reference profile 1 954 left or right for any deviation of the vertical edge from vertical. (If the vertical edge is known to be exactly vertical this step can be skipped and reference profile 1 954 is copied into hypothetical reference profile 0 956. More specifically this step computes the subpixel 50% threshold crossing position of reference profiles 1 and 2, 954 and 952. Then it shifts reference profile 1 left or right by the fractional pixel shift between profiles 2 and 1. Thus, it gives the vertical edge profile expected in the Corner ROI.

Step 6 normalizes the hypothetical reference profile values to between 0 and 1 so that they represent the Vertical Edge Attenuation Profile. Step 7 creates a Corner Reference Profile (for a zero-radius corner) which is corrected for the slopes of the two edges as follows: divide the Corner Profile 942 into two parts (FIG. 34); replace the left side 944 (which is four blur distances wide) with a linear extrapolation of the right side 946 (which can be two blur distances wide). This describes the horizontal edge 948 expected without the corner. Multiply the resultant profile 948 by the Vertical Edge Attenuation Profile (956 normalized) from step 6, giving the Corner Reference Profile.

Step 8 subtracts the Corner Profile 942 from the Corner Reference Profile, and sums the differences to get the total flux difference. Alternatively, the total flux could be computed for each profile and the fluxes subtracted to produce the total flux difference. Step 9 normalizes the total flux difference to the image's contrast range as described earlier herein to get the flux area difference (with units of square pixels).

Step 10 computes the radius of curvature that would give that flux area difference by finding the radius of the circle where the difference in area between the circle and its enclosing square equals the flux area difference times four (because only one of four corners of the square is measured here). For example, radius=sqrt( A (1-pi/4)) (where A is the flux area difference in pixels, and radius is the corner radius in pixels).

Step 11 scales the Corner Radius from pixels to physical units such as microns using a simple scale factor measured or computed based on the optical system, or by using a calibration curve as described earlier herein based on reference measurements derived externally.

An alternate method to compute a radius of curvature is to compute the edge equations (Y=mX+b) for the horizontal and vertical edges from the "50%" threshold intersections in regions 964, 966, 968, and 970. From these equations generate a binary image representing a perfect zero radius corner. Then subtract the measured image or of the corner region 962 from this reference image or profile of it and sum the flux differences from all the pixels. Finally, continue with step 9 above to compute the flux area, radius in pixels, and radius in physical units.

An advantageous step in this alternate method is determining the actual threshold to use, because the threshold should correspond to 50% energy (the integral of the normalized intensity across the edge), not 50% intensity. If the blurring is symmetrical, these values will be identical, but if it is not, the intensity corresponding to 50% energy could be computed in several ways.

By way of example, one method is to compute the integral of the normalized intensities across the edge and pick the position where it crosses 50%, and then interpolate the edge intensity values to that position. This can also be done iteratively as follows: start with a simple 50% threshold, compute the edge position, generate a binary image of the region with that edge position, and compare the total flux in that region with the total flux in the normalized measured image. Then adjust the threshold slightly until the measured image and the binary image have the same total flux.

ILLUMINATION AND INSPECTION EMBODIMENTS

The present invention is useful in conjunction with a wide variety of lighting sources and/or particle microscopes (such as an electron microscope). Considering lighting sources first, it is known in the art to use transmitted illumination, bright field illumination (also called axial illumination), and dark field illumination (also called oblique illumination) to illuminate a medium. Other similar lighting techniques may also be used and the present invention can be used with any of these lighting techniques. For example, it may be desirable to use one of the above lighting techniques on a video inspection machine for inspecting a surface for particulate matter, features, defects and/or line widths. In fact, certain inspection machines are able to employ more than one lighting technique simultaneously, thereby aiding the operator in identifying and sizing particles and features. Because a particular particle or feature may appear best under a certain type of lighting, it can be advantageous to employ more than one lighting technique.

As mentioned above, one lighting technique applicable for use with the present invention is transmitted illumination. Using this technique, light is transmitted through a medium under inspection in order to identify and size various types of features. The transmitted illumination technique is most useful for transparent media because the transparent media will not completely block all of the transmitted light. Media that are suitable for use with transmitted illumination include glass reticles, semiconductor masks, etc., and other transparent media and semi-transparent media. By using transmitted illumination, different features may appear dark or bright. Whereas a spot defect, a chrome line or other opaque substance would appear dark, a hole or absence of a portion of a chrome line on a glass reticle would appear bright because the transmitted light is allowed to pass through the transparent medium.

Another lighting technique is bright field illumination. Unlike transmitted illumination, bright field illumination uses a lighting source that is directed on to, and thus reflected from, the medium under analysis. In a typical setup, a light source is located perpendicular to the lens axis and the light is directed onto the medium axially by way of a reflecting mirror. A camera or other sensing device then picks up the light reflected from the medium. Bright field illumination is advantageous for an opaque surface such as a silicon wafer or other material. For completely or nearly opaque media, transmitted illumination would not be particularly useful because the light would not be transmitted; thus, bright field illumination that uses reflected light can be more advantageous. In addition, bright field illumination may be used with transparent media such as glass, a semiconductor mask or other because such a material, even though able to transmit light, will also reflect light. In general, any reflective medium is suitable for analysis using bright field illumination. In particular, bright field illumination is useful for identifying and sizing excess chrome, dirt or other particulate matter on silicon wafers, chrome surfaces, etc.

With bright field illumination flat surfaces appear bright because they reflect light, while a surface, particle or feature more or less not flat will appear dark because it does not allow light to be reflected back to a sensing device. For example, with bright field illumination spot defects, holes, chrome lines, line extensions, etc. will appear dark, while a flat surface or a missing portion of a chrome line would appear bright. In general, any feature or defect of about less than one micron in size will appear dark because such a feature or defect is close to the wavelength of light. Anything that small would not necessarily appear flat, and thus would appear dark.

Another lighting technique suitable for use with the present invention is dark field illumination. In dark field illumination a lighting source is typically located at an oblique angle from the medium under analysis. In a typical setup, a circular fluorescent light encircles the lens and medium under analysis and provides lighting from the side. As the lighting is from the side, the flat medium will appear dark because it does not necessarily reflect light directly into the lens. However, spot defects, holes, chrome lines, line extensions, etc. will often appear brighter than the dark background because their curved or rough shape allows a certain amount of light to be reflected back up into the lens. For example, a hole or other indent in a flat medium such as a silicon wafer may appear bright, whereas the flat wafer itself would appear dark.

The various embodiments of the inventions described herein are also suitable for use with a variety of particle microscopes such as an electron microscope or a focused ion beam (FIB) microscope. Thus, although many references to light measurements are made herein, and many of the measurements and units are applicable to visible light, the invention is not so limited. References have been made to visible light measurements for ease of presenting the invention. The techniques of the present invention are also applicable to measurements made with other particles as well as electrons. Therefore, references to "wavelength" refer to light wavelengths, electron wavelengths, or wavelengths of other particles used for measurement.

COMPUTER SYSTEM EMBODIMENT

Figure 36:
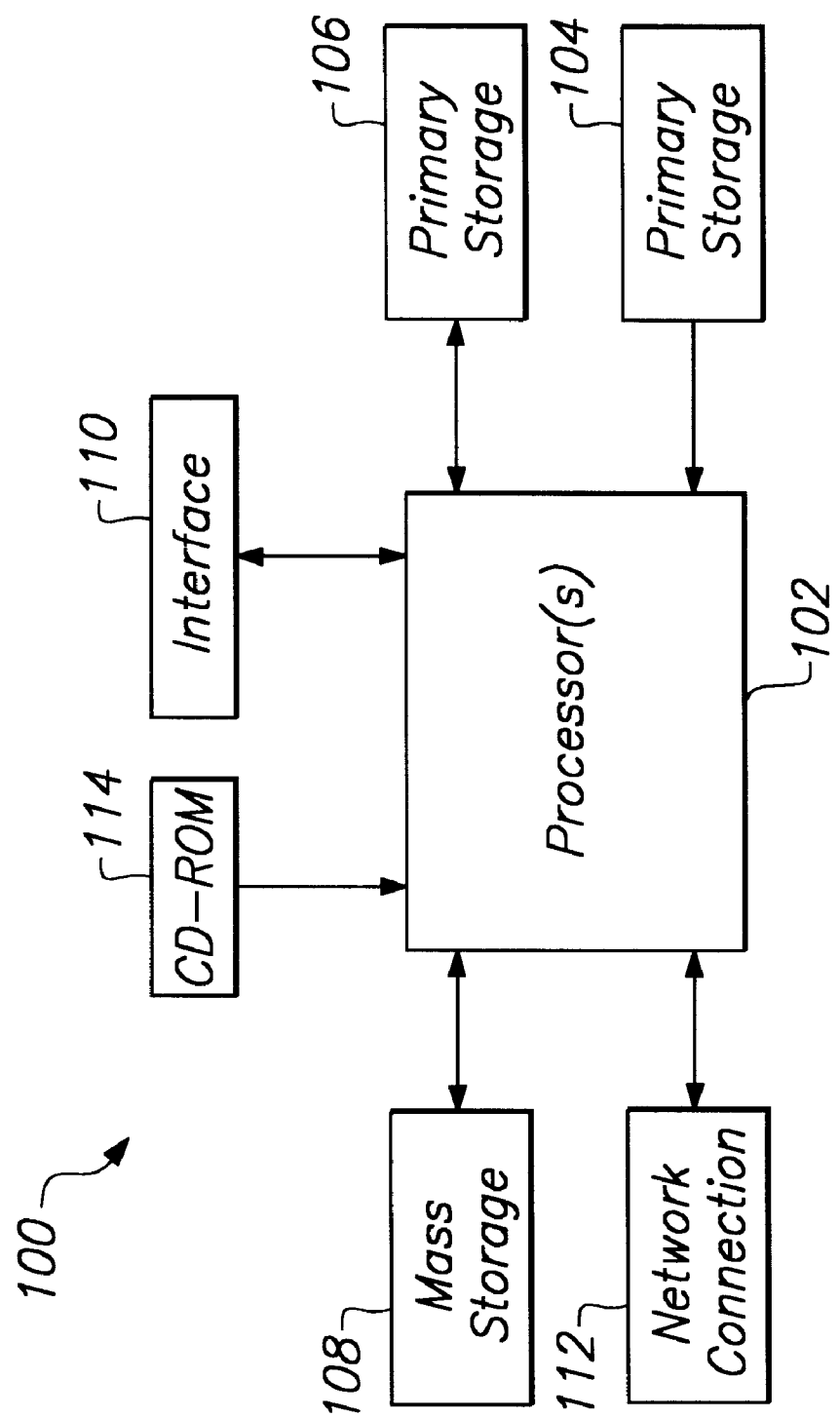
FIG. 36 is a block diagram of a typical computer system suitable for implementing an embodiment of the present invention.

FIG. 36 illustrates a computer system 100 in accordance with an embodiment of the present invention. Computer system 100 includes any number of processors 102 (also referred to as central processing units, or CPUs) that are coupled to storage devices including primary storage 106 (such as random access memory, or RAM) and primary storage 104 (such as a read only memory, or ROM). As is well known in the art, primary storage 104 acts to transfer data and instructions uni-directionally to the CPU and primary storage 106 is used typically to transfer data and instructions in a bidirectional manner. Both of these primary storage devices may include any suitable of the computer-readable media described below. A mass storage device 108 is also coupled bi-directionally to CPU 102 and provides additional data storage capacity and may also include any of the computer-readable media described below. Mass storage device 108 may be used to store programs, data and the like and is typically a secondary storage medium (such as a hard disk) that is slower than primary storage. It will be appreciated that the information retained within mass storage device 108, may, in appropriate cases, be incorporated in standard fashion as part of primary storage 106 as virtual memory. A specific mass storage device such as a CD-ROM 114 passes data uni-directionally to the CPU.

CPU 102 is also coupled to an interface 110 that includes one or more input/output devices such as such as video monitors, track balls, mice, keyboards, microphones, touch-sensitive displays, transducer card readers, magnetic or paper tape readers, tablets, styluses, voice or handwriting recognizers, biometrics readers, or other computers. CPU 102 optionally may be coupled to another computer or telecommunications network using a network connection as shown generally at 112. With such a network connection, it is contemplated that the CPU might receive information from the network, or might output information to the network in the course of performing the above-described method steps. Furthermore, method embodiments of the present invention may execute solely upon CPU 102 or may execute over a network connection such as the Internet in conjunction with a remote CPU that shares a portion of the processing.

In addition, embodiments of the present invention further relate to computer storage products with a computer readable medium that have program code thereon for performing various computer-implemented operations. The media and program code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROM disks; magneto-optical media such as floptical disks; and hardware devices that are specially configured to store and execute program code, such as application-specific integrated circuits (ASICs), programmable logic devices (PLDs) and ROM and RAM devices. Examples of program code include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. For example, the video image input may come from a wide variety of sources. Also, measurements may be taken of a variety of features at the micron level that are present on a variety of media, and not necessarily a photomask. For example, the invention is applicable to biological specimens such as cells, etc. Also, any type of light microscopic may be used as well as an electron microscope or other particle microscope. In addition, the present invention is applicable to measuring a wide variety of features including contacts, vias or other intentional features. Therefore, the described embodiments should be taken as illustrative and not restrictive, and the invention should not be limited to the details given herein but should be defined by the following claims and their full scope of equivalents.

I claim:

1. A computer-implemented method of determining the radius of curvature of a microscopic feature located on a medium, said method comprising:

determining reference flux for a region surrounding a reference corner of said feature;

determining actual flux for a region surrounding an actual corner of said feature;

comparing said reference flux and said actual flux to produce a resulting flux value; and using said resulting flux value to determine said radius of curvature of said feature.

2. A method as recited in claim 1 wherein said radius of curvature is less than about twice the wavelength used in said method.

3. A method as recited in claim 1 wherein said step of determining reference flux includes the sub-step of:

determining vertical and horizontal edges of said actual corner to produce said reference corner.

4. A computer-implemented method of determining the radius of curvature of a microscopic feature located on a medium, said method comprising:

developing a vertical reference profile for a corner region surrounding a corner of said feature;

developing a horizontal reference profile for said corner region surrounding said corner;

combining said vertical reference profile and said horizontal reference profile to produce a corner reference profile; and producing said radius of curvature based upon said corner reference profile and an actual profile of said corner.

5. A method as recited in claim 4 wherein said step of producing includes the substep of:

comparing said corner reference profile to an actual profile of said corner; and determining said radius of curvature based upon the result of said comparing step.

6. A method as recited in claim 4 wherein said step of producing includes the sub-step of:

determining reference flux for said corner reference profile; and determining actual flux for said actual profile.

7. A method as recited in claim 4 wherein said radius of curvature is less than about twice the wavelength used in said method.

8. A mask used in the manufacture of semiconductor devices, said mask resulting from a method of determining the radius of curvature of a microscopic feature located on said mask, said method comprising:

determining reference flux for a region surrounding a reference corner of said feature;

determining actual flux for a region surrounding an actual corner of said feature;

comparing said reference flux and said actual flux to produce a resulting flux value; and using said resulting flux value to determine said radius of curvature of said feature.

9. A mask as recited in claim 8 wherein said radius of curvature is less than about twice the wavelength used in said method.

10. A mask as recited in claim 8 wherein said step of determining reference flux includes the sub-step of:

determining vertical and horizontal edges of said actual corner to produce said reference corner.

11. A mask used in the manufacture of semiconductor devices, said mask resulting from a method of determining the radius of curvature of a microscopic feature located on said mask, said method comprising:

developing a vertical reference profile for a corner region surrounding a corner of said feature;

developing a horizontal reference profile for said corner region surrounding said corner;

combining said vertical reference profile and said horizontal reference profile to produce a corner reference profile; and producing said radius of curvature based upon said corner reference profile and an actual profile of said corner.

12. A mask as recited in claim 11 wherein said step of producing includes the sub-step of:

comparing said corner reference profile to an actual profile of said corner; and determining said radius of curvature based upon the result of said comparing step.

13. A mask as recited in claim 11 wherein said step of producing includes the sub-step of:

determining reference flux for said corner reference profile; and determining actual flux for said actual profile.

14. A mask as recited in claim 11 wherein said radius of curvature is less than about twice the wavelength used in said method.

15. A semiconductor device, said semiconductor device resulting from a method of determining the radius of curvature of a microscopic feature located on a mask, said method comprising:

determining reference flux for a region surrounding a reference corner of said feature;

determining actual flux for a region surrounding an actual corner of said feature;

comparing said reference flux and said actual flux to produce a resulting flux value; and using said resulting flux value to determine said radius of curvature of said feature.

16. A semiconductor device as recited in claim 15 wherein said radius of curvature is less than about twice the wavelength used in said method.

17. A semiconductor device as recited in claim 15 wherein said step of determining reference flux includes the sub-step of:

determining vertical and horizontal edges of said actual corner to produce said reference corner.

18. A semiconductor device, said semiconductor device resulting from a method of determining the radius of curvature of a microscopic feature located on a mask, said method comprising:

developing a vertical reference profile for a corner region surrounding a corner of said feature;

developing a horizontal reference profile for said corner region surrounding said corner;

combining said vertical reference profile and said horizontal reference profile to produce a corner reference profile; and producing said radius of curvature based upon said corner reference profile and an actual profile of said corner.

19. A semiconductor device as recited in claim 18 wherein said step of producing includes the sub-step of:

comparing said corner reference profile to an actual profile of said corner; and determining said radius of curvature based upon the result of said comparing step.

20. A semiconductor device as recited in claim 18 wherein said step of producing includes the sub-step of:

determining reference flux for said corner reference profile; and determining actual flux for said actual profile.

21. A semiconductor device as recited in claim 18 wherein said radius of curvature is less than about twice the wavelength used in said method.

* * * * *